(12) United States Patent
Mohr et al.

(10) Patent No.: US 9,500,633 B2
(45) Date of Patent: Nov. 22, 2016

(54) AUTOMATED MACHINE AND METHOD FOR FRUIT TESTING

(71) Applicants: Charles L. Mohr, Richland, WA (US); Brandt Mohr, Richland, WA (US); Anthony Cottam, Richland, WA (US); Kevin D. Dawes, Richland, WA (US); Preston May, Richland, WA (US); Christopher M. Mulkey, West Richland, WA (US); Duan D. Nguyen, Pasco, WA (US); Marc D. Pirello, Kennewick, WA (US); Michael D. Stordahl, Kennewick, WA (US); James M. Van Corbach, Jr., Sunnyside, WA (US); Erik Von Reis, Kennewick, WA (US)

(72) Inventors: Charles L. Mohr, Richland, WA (US); Brandt Mohr, Richland, WA (US); Anthony Cottam, Richland, WA (US); Kevin D. Dawes, Richland, WA (US); Preston May, Richland, WA (US); Christopher M. Mulkey, West Richland, WA (US); Duan D. Nguyen, Pasco, WA (US); Marc D. Pirello, Kennewick, WA (US); Michael D. Stordahl, Kennewick, WA (US); James M. Van Corbach, Jr., Sunnyside, WA (US); Erik Von Reis, Kennewick, WA (US)

(73) Assignee: Charles L. Mohr, Richland, WA (US)

( * ) Notice: Subject to any disclaimer, the term of this patent is extended or adjusted under 35 U.S.C. 154(b) by 0 days.

(21) Appl. No.: 14/547,072

(22) Filed: Nov. 18, 2014

(65) Prior Publication Data
US 2016/0139099 A1    May 19, 2016

(51) Int. Cl.
*G01N 33/02* (2006.01)
*G01G 17/00* (2006.01)
(Continued)

(52) U.S. Cl.
CPC .......... *G01N 33/025* (2013.01); *G01D 5/3473* (2013.01); *G01G 17/00* (2013.01); *G01N 3/00* (2013.01); *G01N 3/40* (2013.01); *G01N 2203/0094* (2013.01)

(58) Field of Classification Search
CPC .................................................. G01N 33/025
USPC ............................................................. 73/81
See application file for complete search history.

(56) References Cited

U.S. PATENT DOCUMENTS

| 3,406,566 A | 10/1968 | Livingston et al. ............... 73/81 |
| 3,470,737 A | 10/1969 | Fridley ............................ 73/81 |

(Continued)

FOREIGN PATENT DOCUMENTS

FR    EP 0572341 A2 * 12/1993    ........... G01N 33/025

OTHER PUBLICATIONS

("Guidance on Objective Tests to Determine Quality of Fruits and Vegetables Fresh and Dry and Dried Produce." Fruit and Vegetables Guidelines. Organisation for Economic Co-operation and Development, 2009. http://www.oecd.org/tad/code/fruitandvegetablesguidelines.htm. Feb. 4, 2016. Herein after referred to as "OECD".*

*Primary Examiner* — Michael A Lyons
*Assistant Examiner* — Jean Morello
(74) *Attorney, Agent, or Firm* — Randall Danskin PS

(57) ABSTRACT

An improved fruit tester and method provides a plunger intrusion-type mechanism, a precision scale and an associated computer for control of the mechanism and for recordation, presentation and analysis of data sensed by the mechanism. An electrically powered variable speed motor carries an optical encoder to sense rotary direction and speed data, which is transmitted through circuitry to an associated computer for analysis to determine control data to maintain pre-programmed motor function. Computer software determines plunger position and resultant penetration into a fruit at either pre-determined plunger speed or constant plunger resistive pressure in fine increments over the plunger trajectory and stores this data in computer memory. The precision scale is used to determine the weight of the fruit before and after the penetration tests and the difference in weight is used to automatically calculate the Specific juice Content (SJC) of the fruit.

12 Claims, 12 Drawing Sheets

(51) Int. Cl.
  *G01D 5/347* (2006.01)
  *G01N 3/00* (2006.01)
  *G01N 3/40* (2006.01)

(56) References Cited

U.S. PATENT DOCUMENTS

| | | |
|---|---|---|
| 3,732,727 A | 5/1973 | Hinnergardt et al. ............. 73/81 |
| 4,061,020 A | 12/1977 | Fridley et al. .................... 73/81 |
| 4,107,985 A | 8/1978 | Sommer .................. 73/862.633 |
| 4,109,314 A * | 8/1978 | Meyer ................... G01N 35/00 422/77 |
| 4,331,026 A | 5/1982 | Howard et al. ................... 73/81 |
| 4,479,424 A | 10/1984 | Carroll .......................... 99/502 |
| 4,621,523 A | 11/1986 | Shabel et al. ..................... 73/81 |
| 4,657,097 A | 4/1987 | Griffen ......................... 177/211 |
| 4,884,696 A | 12/1989 | Peleg ............................ 209/545 |
| 4,937,924 A | 7/1990 | Leuchtenmuller .............. 28/107 |
| 5,315,879 A | 5/1994 | Crochon et al. ................ 73/818 |
| 5,365,457 A | 11/1994 | Madigosky ................... 364/506 |
| 5,372,030 A | 12/1994 | Prussia et al. .................... 73/37 |
| 5,433,215 A | 7/1995 | Athanasion et al. ......... 128/774 |
| 5,591,902 A | 1/1997 | Castagner ......................... 73/84 |
| 5,616,857 A | 4/1997 | Merck, Jr. et al. ............... 73/82 |
| 5,691,473 A | 11/1997 | Peleg ............................ 73/573 |
| 5,760,312 A | 6/1998 | MacKay et al. ................ 73/818 |

* cited by examiner

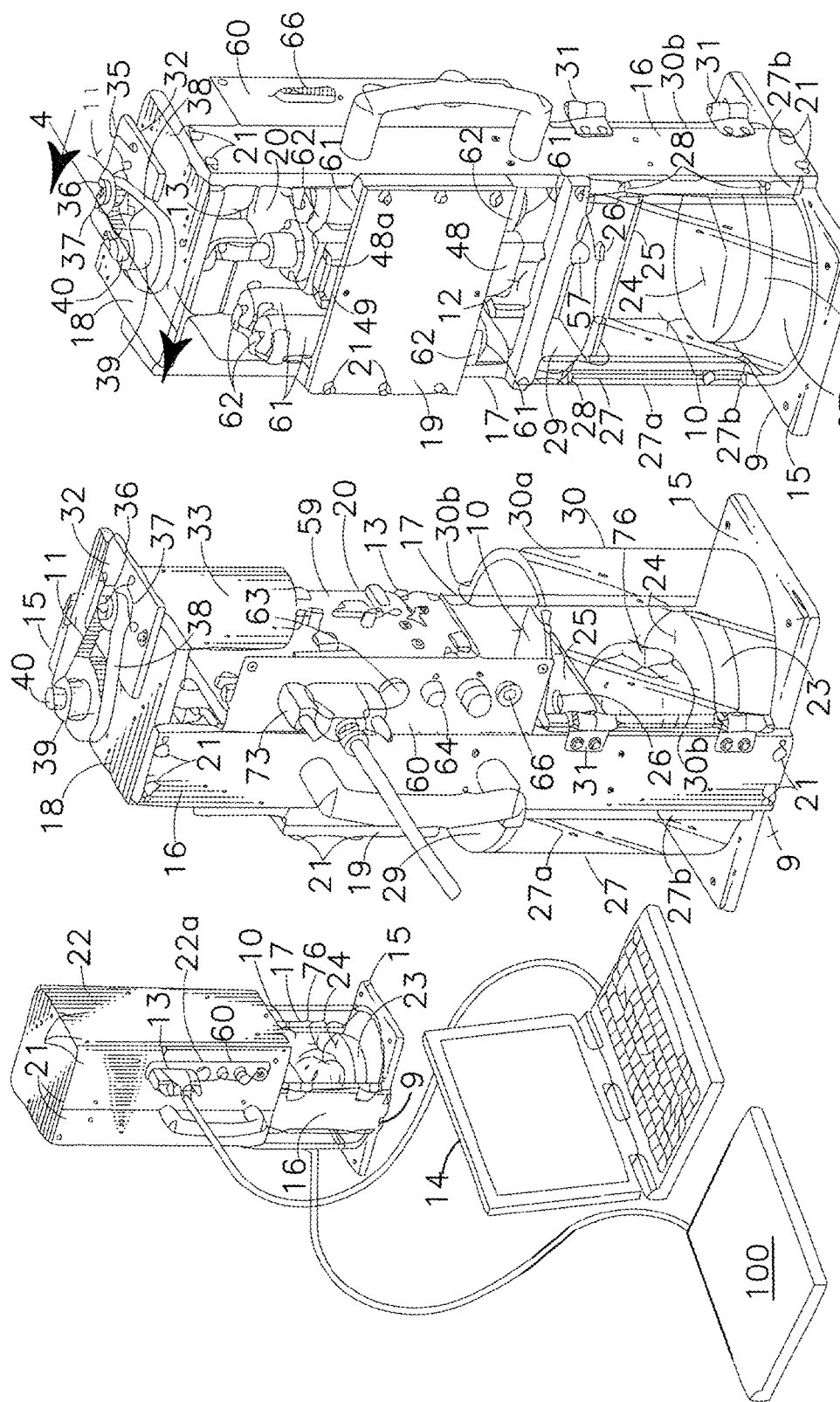

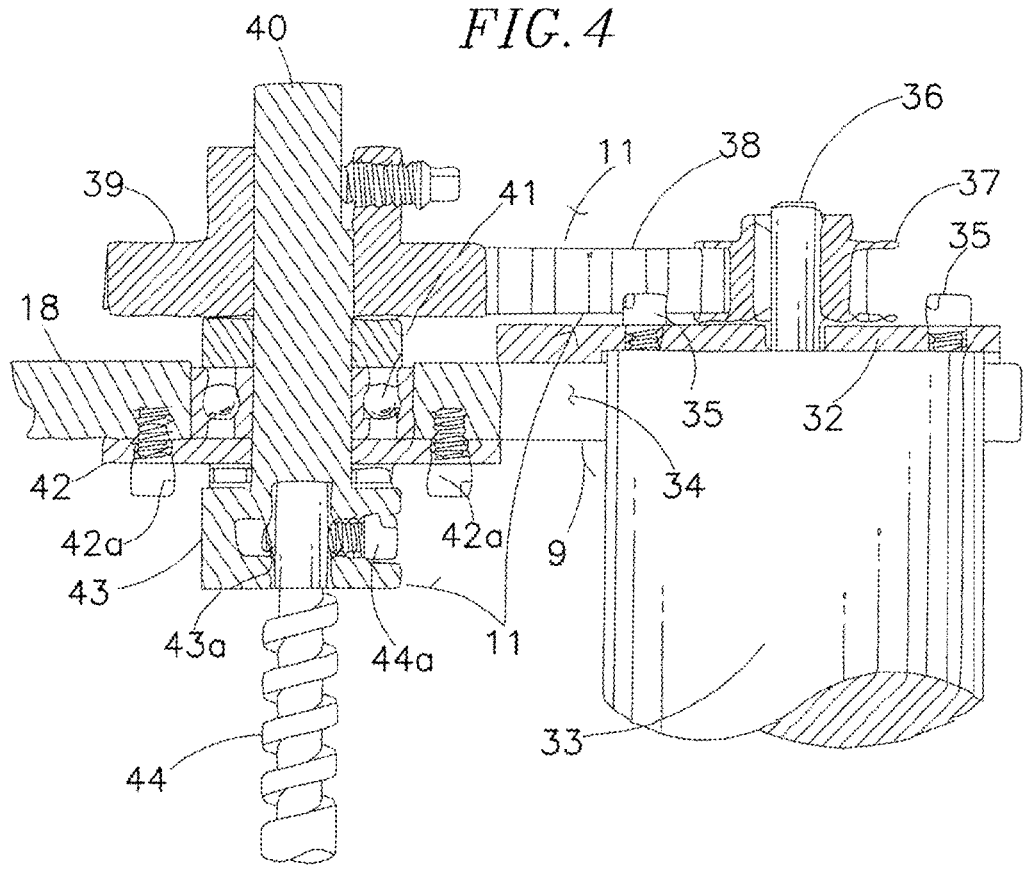
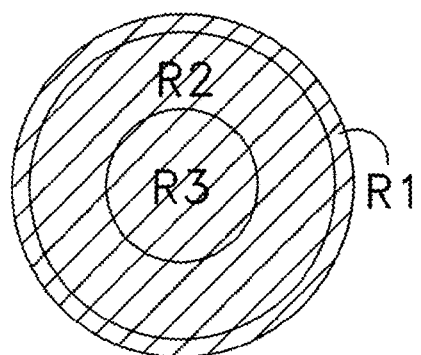

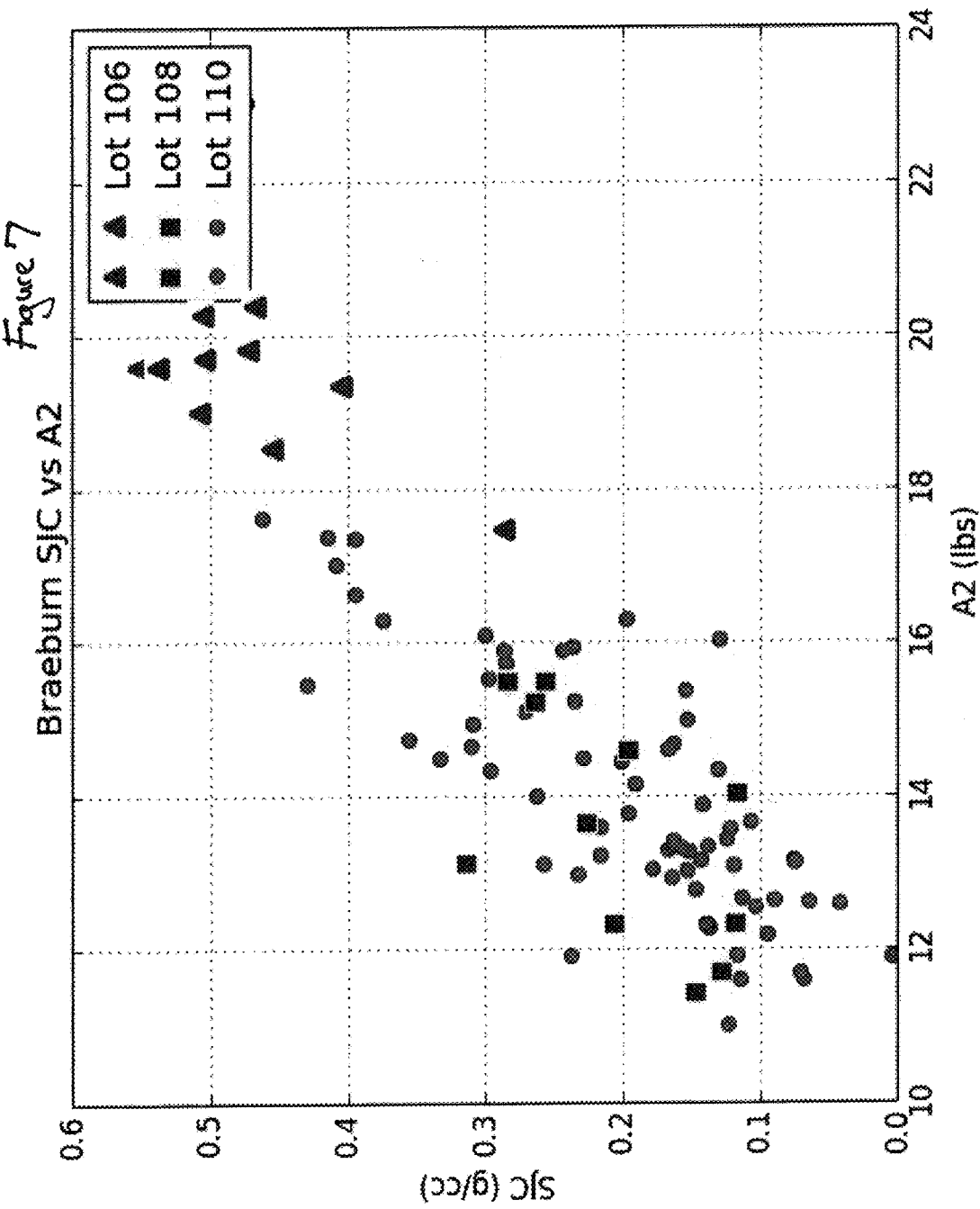

Figure 10A

TABLE A-1
MDT-2 Test Data For Each Apple Group Tested
Gala 1 (8-28-2013)

| apple | QF | CN | A2 | M1 | C0 | E2 | DIA | MDT2S pre (g) | MDT2S post (g) | CPS pre (g) | CPS post (g) | JUICE (MDT2S) | JUICE (CPS) | subj. juice1 | subj. juice2 | tilt1 | tilt2 |
|---|---|---|---|---|---|---|---|---|---|---|---|---|---|---|---|---|---|
| 1 | 23.8 | 194.3 | 15.5 | 12.9 | 0.010 | 11.3 | 3.10 | 222.755 | 221.035 | 222.790 | 221.120 | 0.1933 | 0.1876 | 8 | 8 | 4 | 7 |
| 1 | 8.1 | 118.4 | 14.8 | 11.6 | 0.020 | 15.9 | 3.08 | 222.755 | 221.035 | 222.790 | 221.120 | 0.1933 | 0.1876 | 8 | 8 | 4 | 7 |
| 1 | 15.2 | 186.5 | 14.6 | 11.8 | 0.015 | 12.7 | 3.03 | 222.755 | 221.035 | 222.790 | 221.120 | 0.1933 | 0.1876 | 8 | 8 | 4 | 7 |
| 1 | 24.6 | 145.2 | 15.0 | 13.4 | 0.021 | 17.9 | 3.05 | 222.755 | 221.035 | 222.790 | 221.120 | 0.1933 | 0.1876 | 8 | 8 | 4 | 7 |
| 2 | 91.9 | 299.7 | 18.5 | 15.0 | 0.000 | 19.6 | 2.98 | 237.441 | 234.733 | 237.110 | 234.670 | 0.3118 | 0.2809 | 6 | 6 | 6 | 4 |
| 2 | 92.9 | 256.9 | 18.5 | 15.4 | 0.000 | 22.3 | 2.96 | 237.441 | 234.733 | 237.110 | 234.670 | 0.3118 | 0.2809 | 6 | 6 | 6 | 4 |
| 2 | 110.3 | 478.6 | 19.1 | 15.7 | 0.000 | 22.2 | 3.05 | 237.441 | 234.733 | 237.110 | 234.670 | 0.3118 | 0.2809 | 6 | 6 | 6 | 4 |
| 2 | 100.1 | 283.9 | 18.9 | 14.9 | 0.000 | 23.3 | 2.99 | 237.441 | 234.733 | 237.110 | 234.670 | 0.3118 | 0.2809 | 6 | 7 | 6 | 4 |
| 3 | 73.4 | 270.5 | 17.3 | 15.3 | 0.000 | 15.8 | 2.97 | 215.137 | 212.018 | 215.230 | 212.480 | 0.3557 | 0.3136 | 8 | 7 | 5 | 5 |
| 3 | 70.3 | 265.2 | 17.5 | 14.2 | 0.001 | 16.4 | 2.96 | 215.137 | 212.018 | 215.230 | 212.480 | 0.3557 | 0.3136 | 8 | 7 | 5 | 5 |
| 3 | 62.3 | 185.5 | 17.4 | 14.5 | 0.000 | 18.1 | 3.07 | 215.137 | 212.018 | 215.230 | 212.480 | 0.3557 | 0.3136 | 8 | 7 | 5 | 5 |
| 3 | 62.9 | 197.0 | 17.0 | 13.9 | 0.002 | 19.5 | 3.10 | 215.137 | 212.018 | 215.230 | 212.480 | 0.3557 | 0.3136 | 8 | 7 | 5 | 5 |
| 4 | 51.5 | 177.1 | 16.8 | 14.3 | 0.002 | 16.4 | 3.00 | 221.038 | 217.852 | 220.970 | 218.440 | 0.3649 | 0.2897 | 6 | 7 | 4 | 6 |
| 4 | 55.3 | 120.8 | 17.6 | 15.0 | 0.000 | 18.7 | 2.93 | 221.038 | 217.852 | 220.970 | 218.440 | 0.3649 | 0.2897 | 6 | 7 | 4 | 6 |
| 4 | 64.1 | 134.7 | 18.2 | 15.5 | 0.000 | 19.6 | 3.06 | 221.038 | 217.852 | 220.970 | 218.440 | 0.3649 | 0.2897 | 6 | 7 | 4 | 6 |
| 4 | 71.5 | 264.9 | 17.0 | 14.5 | 0.001 | 17.3 | 3.10 | 221.038 | 217.852 | 220.970 | 218.440 | 0.3649 | 0.2897 | 6 | 7 | 4 | 6 |
| 5 | 96.0 | 324.6 | 18.3 | 14.5 | 0.002 | 21.6 | 2.96 | 225.074 | 222.566 | 224.960 | 222.900 | 0.2814 | 0.2311 | 6 | 6 | 3 | 4 |
| 5 | 46.9 | 170.1 | 16.9 | 15.7 | 0.002 | 13.0 | 3.02 | 225.074 | 222.566 | 224.960 | 222.900 | 0.2814 | 0.2311 | 6 | 6 | 3 | 4 |
| 5 | 69.1 | 254.1 | 17.0 | 14.5 | 0.002 | 17.5 | 3.14 | 225.074 | 222.566 | 224.960 | 222.900 | 0.2814 | 0.2311 | 6 | 6 | 3 | 4 |
| 5 | 69.8 | 206.4 | 17.2 | 15.6 | 0.003 | 19.3 | 3.17 | 225.074 | 222.566 | 224.960 | 222.900 | 0.2814 | 0.2311 | 6 | 6 | 3 | 4 |
| 6 | 70.1 | 240.2 | 17.8 | 13.3 | 0.007 | 20.8 | 3.08 | 221.868 | 220.784 | 222.010 | 220.430 | 0.1228 | 0.1789 | 7 | 7 | 6 | 7 |
| 6 | 60.1 | 243.0 | 16.6 | 12.8 | 0.009 | 19.7 | 3.05 | 221.868 | 220.784 | 222.010 | 220.430 | 0.1228 | 0.1789 | 7 | 7 | 6 | 7 |
| 6 | 84.5 | 463.0 | 17.0 | 13.7 | 0.004 | 19.6 | 3.07 | 221.868 | 220.784 | 222.010 | 220.430 | 0.1228 | 0.1789 | 7 | 7 | 6 | 7 |
| 6 | 75.0 | 300.3 | 17.4 | 13.9 | 0.006 | 18.2 | 3.00 | 221.868 | 220.784 | 222.010 | 220.430 | 0.1228 | 0.1789 | 7 | 7 | 6 | 7 |
| 7 | 102.7 | 259.1 | 20.1 | 15.3 | 0.000 | 23.7 | 2.99 | 216.792 | 213.624 | 216.820 | 213.850 | 0.3682 | 0.3452 | 5 | 7 | 5 | 6 |
| 7 | 106.3 | 275.9 | 20.1 | 15.5 | 0.000 | 23.8 | 3.05 | 216.792 | 213.624 | 216.820 | 213.850 | 0.3682 | 0.3452 | 5 | 7 | 5 | 6 |
| 7 | 115.5 | 403.8 | 21.3 | 17.6 | 0.009 | 18.7 | 2.92 | 216.792 | 213.624 | 216.820 | 213.850 | 0.3682 | 0.3452 | 5 | 7 | 5 | 6 |
| 7 | 83.4 | 218.5 | 20.3 | 16.8 | 0.000 | 17.1 | 2.90 | 216.792 | 213.624 | 216.820 | 213.850 | 0.3682 | 0.3452 | 5 | 7 | 5 | 6 |

Figure 10B

| | QF | CN | A2 | M1 | C0 | E2 | DiA | MDT2S pre (g) | MDT2S post (g) | CPS pre (g) | CPS post (g) |
|---|---|---|---|---|---|---|---|---|---|---|---|
| avg | 70.0 | 247.8 | 17.6 | 14.5 | 0.004 | 18.6 | 3.03 | 222.872 | 220.373 | 222.941 | 220.556 |
| std. dev. | 27.8 | 89.0 | 1.6 | 1.3 | 0.006 | 3.1 | 0.07 | 6.743 | 6.901 | 6.817 | 6.758 |

| | | | | | | | | | | | | JUICE (MDT2S) | JUICE (CPS) |
|---|---|---|---|---|---|---|---|---|---|---|---|---|---|
| avg | | | | | | | | | | | | 0.2854 | 0.2610 |
| std. dev. | | | | | | | | | | | | 0.0876 | 0.0587 |

| | | | | | | | | | |
|---|---|---|---|---|---|---|---|---|---|
| avg | 6.6 | 6.9 | 4.7 | 5.6 | | | | | |
| std. dev. | 1.0 | 0.5 | 1.0 | 1.2 | | | | | |

Gala 2 (9-04-2013)

| apple | QF | CN | A2 | M1 | C0 | E2 | DiA | MDT2S pre (g) | MDT2S post (g) | CPS pre (g) | CPS post (g) | JUICE (MDT2S) | JUICE (CPS) | subj. juice1 | subj. juice2 | tilt1 | tilt2 |
|---|---|---|---|---|---|---|---|---|---|---|---|---|---|---|---|---|---|
| 1 | 73.5 | 224.4 | 18.5 | 15.9 | 0.000 | 16.4 | 2.90 | 188.358 | 186.070 | 188.330 | 186.020 | 0.2782 | 0.2809 | 8 | 6 | 8 | 5 |
| 1 | 62.0 | 171.8 | 17.3 | 15.4 | 0.002 | 18.5 | 2.84 | 188.358 | 186.070 | 188.330 | 186.020 | 0.2782 | 0.2809 | 8 | 6 | 8 | 5 |
| 1 | 59.2 | 146.8 | 18.2 | 15.1 | 0.003 | 18.4 | 2.82 | 188.358 | 186.070 | 188.330 | 186.020 | 0.2782 | 0.2809 | 8 | 6 | 8 | 5 |
| 1 | 73.2 | 172.2 | 18.3 | 15.9 | 0.000 | 19.9 | 2.83 | 188.358 | 186.070 | 188.330 | 186.020 | 0.2782 | 0.2809 | 8 | 6 | 8 | 5 |
| 2 | 74.6 | 186.5 | 17.7 | 15.1 | 0.000 | 21.4 | 2.91 | 201.428 | 199.175 | 201.880 | 199.250 | 0.2640 | 0.3082 | 7 | 8 | 7 | 8 |
| 2 | 97.4 | 275.8 | 18.8 | 17.2 | 0.000 | 19.8 | 2.89 | 201.428 | 199.175 | 201.880 | 199.250 | 0.2640 | 0.3082 | 7 | 8 | 7 | 8 |
| 2 | 102.1 | 287.6 | 19.3 | 15.7 | 0.000 | 22.2 | 3.01 | 201.428 | 199.175 | 201.880 | 199.250 | 0.2640 | 0.3082 | 7 | 8 | 7 | 8 |
| 2 | 108.0 | 346.5 | 18.7 | 14.5 | 0.000 | 23.5 | 2.99 | 201.428 | 199.175 | 201.880 | 199.250 | 0.2640 | 0.3082 | 7 | 8 | 7 | 8 |
| 3 | 96.5 | 221.7 | 19.9 | 15.6 | 0.000 | 23.7 | 2.84 | 193.566 | 191.475 | 193.880 | 191.540 | 0.2495 | 0.2791 | 8 | 7 | 7 | 5 |
| 3 | 87.9 | 181.1 | 20.3 | 16.6 | 0.000 | 21.2 | 2.85 | 193.566 | 191.475 | 193.880 | 191.540 | 0.2495 | 0.2791 | 8 | 7 | 7 | 5 |
| 3 | 63.7 | 120.8 | 18.5 | 16.9 | 0.000 | 18.2 | 2.92 | 193.566 | 191.475 | 193.880 | 191.540 | 0.2495 | 0.2791 | 8 | 7 | 7 | 5 |
| 3 | 119.2 | 362.2 | 20.1 | 16.4 | 0.000 | 23.4 | 2.97 | 193.566 | 191.475 | 193.880 | 191.540 | 0.2495 | 0.2791 | 8 | 7 | 7 | 5 |
| 4 | 89.6 | 361.4 | 17.3 | 14.0 | 0.002 | 19.7 | 2.93 | 203.179 | 203.179 | 205.840 | 203.630 | 0.2713 | 0.2622 | 7 | 7 | 8 | 7 |
| 4 | 90.3 | 477.7 | 16.9 | 14.4 | 0.002 | 20.0 | 2.98 | 203.179 | 203.179 | 205.840 | 203.630 | 0.2713 | 0.2622 | 7 | 7 | 8 | 7 |
| 4 | 55.8 | 177.9 | 16.7 | 13.9 | 0.004 | 19.0 | 2.88 | 203.179 | 203.179 | 205.840 | 203.630 | 0.2713 | 0.2622 | 7 | 7 | 8 | 7 |
| 4 | 93.8 | 292.3 | 18.5 | 14.9 | 0.000 | 20.8 | 2.87 | 203.179 | 203.179 | 205.840 | 203.630 | 0.2713 | 0.2622 | 7 | 7 | 8 | 7 |
| 5 | 115.0 | 373.0 | 19.2 | 16.2 | 0.000 | 23.2 | 2.80 | 189.713 | 186.986 | 189.880 | 186.960 | 0.3348 | 0.3586 | 7 | 7 | 6 | 6 |
| 5 | 120.6 | 385.5 | 19.6 | 15.9 | 0.000 | 25.1 | 2.78 | 189.713 | 186.986 | 189.880 | 186.960 | 0.3348 | 0.3586 | 7 | 7 | 6 | 6 |
| 5 | 83.5 | 228.5 | 18.3 | 15.2 | 0.000 | 21.0 | 2.81 | 189.713 | 186.986 | 189.880 | 186.960 | 0.3348 | 0.3586 | 7 | 7 | 6 | 6 |
| 5 | 133.8 | 347.9 | 20.8 | 18.3 | 0.000 | 25.1 | 2.82 | 189.713 | 186.986 | 189.880 | 186.960 | 0.3348 | 0.3586 | 7 | 7 | 6 | 6 |
| 6 | 68.9 | 164.8 | 17.4 | 15.5 | 0.000 | 20.5 | 2.90 | 197.007 | 195.172 | 197.640 | 195.360 | 0.2197 | 0.2731 | 7 | 7 | 7 | 8 |
| 6 | 89.3 | 222.3 | 18.4 | 15.4 | 0.000 | 23.1 | 2.91 | 197.007 | 195.172 | 197.640 | 195.360 | 0.2197 | 0.2731 | 7 | 7 | 7 | 8 |
| 6 | 74.7 | 192.6 | 17.6 | 15.6 | 0.000 | 20.5 | 2.84 | 197.007 | 195.172 | 197.640 | 195.360 | 0.2197 | 0.2731 | 7 | 7 | 7 | 8 |
| 6 | 88.2 | 304.1 | 16.9 | 14.7 | 0.000 | 20.4 | 2.83 | 197.007 | 195.172 | 197.640 | 195.360 | 0.2197 | 0.2731 | 7 | 7 | 7 | 8 |

Figure 10C

| | | | | | | | | | | | | | | | | | | |
|---|---|---|---|---|---|---|---|---|---|---|---|---|---|---|---|---|---|---|
| 7 | 102.8 | 177.4 | 21.5 | 20.2 | 0.000 | 20.5 | 2.89 | 197.601 | 195.299 | 197.790 | 195.330 | 0.2735 | 0.2922 | 8 | 7 | 8 | 6 |
| 7 | 91.0 | 238.3 | 20.1 | 16.1 | 0.000 | 19.7 | 2.85 | 197.601 | 195.299 | 197.790 | 195.330 | 0.2735 | 0.2922 | 8 | 7 | 8 | 6 |
| 7 | 81.0 | 203.4 | 19.3 | 17.8 | 0.000 | 17.0 | 2.93 | 197.601 | 195.299 | 197.790 | 195.330 | 0.2735 | 0.2922 | 8 | 7 | 8 | 6 |
| 7 | 112.8 | 295.6 | 21.1 | 17.8 | 0.000 | 20.5 | 2.95 | 197.601 | 195.299 | 197.790 | 195.330 | 0.2735 | 0.2922 | 8 | 7 | 8 | 6 |
| 8 | 82.4 | 215.9 | 19.5 | 15.9 | 0.000 | 19.1 | 2.98 | 202.311 | 199.433 | 202.260 | 199.520 | 0.3454 | 0.3288 | 8 | 8 | 8 | 8 |
| 8 | 98.7 | 386.6 | 19.1 | 15.8 | 0.000 | 18.0 | 2.93 | 202.311 | 199.433 | 202.260 | 199.520 | 0.3454 | 0.3288 | 8 | 8 | 8 | 8 |
| 8 | 98.6 | 285.2 | 19.3 | 17.0 | 0.000 | 19.2 | 2.78 | 202.311 | 199.433 | 202.260 | 199.520 | 0.3454 | 0.3288 | 8 | 8 | 8 | 8 |
| 8 | 63.3 | 157.5 | 18.7 | 15.0 | 0.000 | 17.9 | 2.82 | 202.311 | 199.433 | 202.260 | 199.520 | 0.3454 | 0.3288 | 8 | 8 | 8 | 8 |
| 9 | 122.0 | 292.9 | 21.7 | 19.0 | 0.000 | 21.6 | 2.81 | 196.700 | 193.995 | 197.320 | 194.400 | 0.3291 | 0.3553 | 8 | 5 | 8 | 5 |
| 9 | 96.4 | 239.4 | 19.4 | 16.2 | 0.000 | 22.4 | 2.81 | 196.700 | 193.995 | 197.320 | 194.400 | 0.3291 | 0.3553 | 8 | 5 | 8 | 5 |
| 9 | 112.4 | 264.2 | 20.0 | 18.0 | 0.000 | 23.4 | 2.86 | 196.700 | 193.995 | 197.320 | 194.400 | 0.3291 | 0.3553 | 8 | 5 | 8 | 5 |
| 9 | 127.7 | 392.3 | 20.3 | 18.5 | 0.000 | 23.1 | 2.85 | 196.700 | 193.995 | 197.320 | 194.400 | 0.3291 | 0.3553 | 8 | 5 | 8 | 5 |
| 10 | 92.2 | 267.8 | 18.4 | 16.3 | 0.000 | 20.1 | 2.94 | 203.622 | 202.543 | 204.240 | 202.470 | 0.1263 | 0.2070 | 8 | 7 | 9 | 6 |
| 10 | 57.7 | 247.6 | 16.2 | 14.1 | 0.034 | 15.8 | 2.93 | 203.622 | 202.543 | 204.240 | 202.470 | 0.1263 | 0.2070 | 8 | 7 | 9 | 6 |
| 10 | 79.2 | 279.0 | 19.5 | 15.8 | 0.000 | 15.2 | 2.99 | 203.622 | 202.543 | 204.240 | 202.470 | 0.1263 | 0.2070 | 8 | 7 | 9 | 6 |
| 10 | 30.4 | 147.6 | 15.8 | 12.8 | 0.008 | 15.5 | 2.98 | 203.622 | 202.543 | 204.240 | 202.470 | 0.1263 | 0.2070 | 8 | 7 | 9 | 6 |
| avg | 89.2 | 257.9 | 18.8 | 16.0 | 0.001 | 20.4 | 2.89 | 197.577 | 195.333 | 197.906 | 195.448 | 0.2692 | 0.2945 | 7.6 | 6.8 | 7.9 | 6.4 |
| std. dev. | 22.0 | 82.7 | 1.4 | 1.5 | 0.001 | 2.5 | 0.06 | 5.477 | 5.633 | 5.573 | 5.698 | 0.0809 | 0.0433 | 0.5 | 0.9 | 0.5 | 1.2 |

Gala 3 (9-11-2013)

| apple | QF | CN | A2 | M1 | C0 | E2 | DIA | MDT2S pre (g) | MDT2S post (g) | CP5 pre (g) | CP5 post (g) | JUICE (MDT2S) | JUICE (CP5) | subj. juice1 | subj. juice2 | tilt1 | tilt2 |
|---|---|---|---|---|---|---|---|---|---|---|---|---|---|---|---|---|---|
| 1 | 90.9 | 607.3 | 17.6 | 17.9 | 0.000 | 14.1 | 2.99 | 189.400 | 186.519 | 189.330 | 186.360 | 0.3519 | 0.3628 | 7 | 7 | 6 | 6 |
| 1 | 91.2 | 215.7 | 18.6 | 16.3 | 0.000 | 22.7 | 2.96 | 189.400 | 186.519 | 189.330 | 186.360 | 0.3519 | 0.3628 | 7 | 7 | 6 | 6 |
| 1 | 106.9 | 464.8 | 18.8 | 17.0 | 0.001 | 20.0 | 3.07 | 189.400 | 186.519 | 189.330 | 186.360 | 0.3519 | 0.3628 | 7 | 7 | 6 | 6 |
| 1 | 59.3 | 103.5 | 18.4 | 16.2 | 0.000 | 18.7 | 3.03 | 189.400 | 186.519 | 189.330 | 186.360 | 0.3519 | 0.3628 | 7 | 7 | 6 | 6 |
| 2 | 82.1 | 170.3 | 19.5 | 16.1 | 0.000 | 21.6 | 2.97 | 191.093 | 188.469 | 190.650 | 188.900 | 0.3127 | 0.2086 | 6 | 7 | 6 | 8 |
| 2 | 76.4 | 147.7 | 18.8 | 17.0 | 0.000 | 20.5 | 2.96 | 191.093 | 188.469 | 190.650 | 188.900 | 0.3127 | 0.2086 | 6 | 7 | 6 | 8 |
| 2 | 64.5 | 106.8 | 18.5 | 16.0 | 0.002 | 21.0 | 3.05 | 191.093 | 188.469 | 190.650 | 188.900 | 0.3127 | 0.2086 | 6 | 7 | 6 | 8 |
| 2 | 129.1 | 312.8 | 21.6 | 17.9 | 0.000 | 24.5 | 3.08 | 191.093 | 188.469 | 190.650 | 188.900 | 0.3127 | 0.2086 | 6 | 7 | 6 | 8 |

Figure 10B

| | | | | | | | | | | | | | | |
|---|---|---|---|---|---|---|---|---|---|---|---|---|---|---|
| 3 | 89.0 | 286.9 | 17.5 | 16.1 | 0.000 | 19.1 | 2.78 | 206.012 | 206.630 | 208.770 | 206.160 | 0.3056 | 0.3046 | 8 | 7 | 7 | 6 |
| 3 | 75.9 | 203.7 | 17.0 | 16.0 | 0.000 | 20.4 | 2.83 | 206.012 | 206.630 | 208.770 | 206.160 | 0.3056 | 0.3046 | 8 | 7 | 7 | 6 |
| 3 | 101.9 | 337.0 | 17.6 | 15.9 | 0.000 | 20.8 | 3.07 | 206.012 | 206.630 | 208.770 | 206.160 | 0.3056 | 0.3046 | 8 | 7 | 7 | 6 |
| 3 | 68.5 | 195.2 | 17.6 | 14.6 | 0.003 | 20.3 | 3.05 | 206.012 | 206.630 | 208.770 | 206.160 | 0.3056 | 0.3046 | 8 | 7 | 7 | 6 |
| 4 | 54.0 | 213.5 | 16.3 | 14.9 | 0.000 | 14.2 | 3.13 | 191.264 | 193.229 | 193.420 | 191.000 | 0.2401 | 0.2956 | 8 | 6 | 7 | 9 |
| 4 | 45.9 | 144.8 | 16.7 | 15.0 | 0.003 | 16.2 | 3.14 | 191.264 | 193.229 | 193.420 | 191.000 | 0.2401 | 0.2956 | 8 | 6 | 7 | 9 |
| 4 | 30.8 | 134.3 | 16.6 | 16.7 | 0.000 | 8.1 | 2.92 | 191.264 | 193.229 | 193.420 | 191.000 | 0.2401 | 0.2956 | 8 | 6 | 7 | 9 |
| 4 | 56.8 | 145.5 | 17.4 | 15.9 | 0.001 | 17.2 | 2.94 | 191.264 | 193.229 | 193.420 | 191.000 | 0.2401 | 0.2956 | 8 | 6 | 7 | 9 |
| 5 | 93.3 | 244.4 | 19.1 | 17.6 | 0.000 | 19.5 | 2.99 | 195.529 | 198.380 | 198.860 | 196.020 | 0.3391 | 0.3377 | 8 | 7 | 7 | 3 |
| 5 | 75.8 | 167.7 | 18.8 | 17.3 | 0.000 | 18.7 | 2.98 | 195.529 | 198.380 | 198.860 | 196.020 | 0.3391 | 0.3377 | 8 | 7 | 7 | 3 |
| 5 | 95.8 | 285.8 | 18.9 | 17.8 | 0.000 | 17.6 | 3.09 | 195.529 | 198.380 | 198.860 | 196.020 | 0.3391 | 0.3377 | 8 | 7 | 7 | 3 |
| 5 | 107.9 | 338.7 | 18.5 | 17.5 | 0.000 | 19.7 | 3.11 | 195.529 | 198.380 | 198.860 | 196.020 | 0.3391 | 0.3377 | 8 | 7 | 7 | 3 |
| 6 | 77.8 | 217.9 | 18.8 | 15.4 | 0.003 | 19.6 | 2.98 | 166.720 | 168.356 | 168.770 | 166.650 | 0.2035 | 0.2638 | 6 | 6 | 7 | 5 |
| 6 | 30.9 | 161.0 | 16.1 | 14.6 | 0.006 | 11.5 | 2.94 | 166.720 | 168.356 | 168.770 | 166.650 | 0.2035 | 0.2638 | 6 | 6 | 7 | 5 |
| 6 | 38.7 | 140.8 | 17.0 | 14.4 | 0.002 | 13.8 | 3.10 | 166.720 | 168.356 | 168.770 | 166.650 | 0.2035 | 0.2638 | 6 | 6 | 7 | 5 |
| 6 | 58.0 | 151.8 | 18.3 | 14.1 | 0.005 | 19.5 | 3.10 | 166.720 | 168.356 | 168.770 | 166.650 | 0.2035 | 0.2638 | 6 | 6 | 7 | 5 |
| 7 | 91.9 | 356.3 | 17.2 | 14.6 | 0.002 | 20.0 | 2.99 | 196.162 | 198.402 | 197.920 | 196.210 | 0.2683 | 0.2049 | 6 | 3 | 7 | 3 |
| 7 | 34.8 | 155.9 | 15.7 | 14.3 | 0.003 | 13.4 | 2.97 | 196.162 | 198.402 | 197.920 | 196.210 | 0.2683 | 0.2049 | 6 | 3 | 7 | 3 |
| 7 | 56.5 | 120.9 | 18.1 | 14.8 | 0.001 | 13.2 | 2.93 | 196.162 | 198.402 | 197.920 | 196.210 | 0.2683 | 0.2049 | 6 | 3 | 7 | 3 |
| 7 | 46.4 | 168.8 | 16.3 | 13.4 | 0.007 | 18.6 | 2.95 | 196.162 | 198.402 | 197.920 | 196.210 | 0.2683 | 0.2049 | 6 | 3 | 7 | 3 |
| 8 | 58.6 | 236.1 | 16.4 | 14.7 | 0.011 | 17.9 | 2.91 | 197.956 | 200.620 | 200.790 | 198.520 | 0.3109 | 0.2649 | 6 | 8 | 6 | 6 |
| 8 | 43.8 | 95.3 | 17.2 | 14.7 | 0.003 | 18.0 | 2.97 | 197.956 | 200.620 | 200.790 | 198.520 | 0.3109 | 0.2649 | 6 | 8 | 6 | 6 |
| 8 | 58.7 | 205.9 | 16.3 | 14.1 | 0.004 | 18.7 | 3.06 | 197.956 | 200.620 | 200.790 | 198.520 | 0.3109 | 0.2649 | 6 | 8 | 6 | 6 |
| 8 | 54.6 | 174.4 | 17.3 | 14.0 | 0.003 | 17.9 | 3.09 | 197.956 | 200.620 | 200.790 | 198.520 | 0.3109 | 0.2649 | 6 | 8 | 6 | 6 |
| 9 | 64.9 | 144.0 | 18.7 | 16.1 | 0.000 | 17.9 | 3.10 | 205.173 | 207.302 | 207.610 | 205.260 | 0.2464 | 0.2720 | 6 | 8 | 8 | 8 |
| 9 | 63.0 | 143.0 | 17.0 | 15.8 | 0.000 | 19.8 | 3.14 | 205.173 | 207.302 | 207.610 | 205.260 | 0.2464 | 0.2720 | 6 | 8 | 8 | 8 |
| 9 | 98.1 | 263.9 | 18.2 | 17.3 | 0.000 | 21.4 | 3.02 | 205.173 | 207.302 | 207.610 | 205.260 | 0.2464 | 0.2720 | 6 | 8 | 8 | 8 |
| 9 | 90.7 | 236.2 | 17.9 | 16.5 | 0.000 | 18.1 | 3.04 | 205.173 | 207.302 | 207.610 | 205.260 | 0.2464 | 0.2720 | 6 | 8 | 8 | 8 |
| 10 | 88.4 | 216.6 | 19.1 | 15.6 | 0.000 | 22.1 | 3.03 | 197.549 | 199.153 | 199.320 | 197.370 | 0.1885 | 0.2290 | 6 | 6 | 7 | 7 |
| 10 | 60.0 | 175.3 | 15.8 | 16.0 | 0.003 | 18.3 | 3.01 | 197.549 | 199.153 | 199.320 | 197.370 | 0.1885 | 0.2290 | 6 | 6 | 7 | 7 |
| 10 | 58.7 | 148.5 | 17.0 | 17.2 | 0.002 | 16.7 | 3.06 | 197.549 | 199.153 | 199.320 | 197.370 | 0.1885 | 0.2290 | 6 | 6 | 7 | 7 |
| 10 | 55.3 | 147.8 | 16.6 | 15.5 | 0.002 | 18.1 | 3.01 | 197.549 | 199.153 | 199.320 | 197.370 | 0.1885 | 0.2290 | 6 | 6 | 7 | 7 |

Figure 10E

|  | 70.7 | 213.7 | 17.7 | 15.8 | 0.002 | 18.4 | 3.01 | 195.457 | 193.135 | 195.544 | 193.245 | 0.2767 | 0.2744 | 6.7 | 6.5 | 6.8 | 6.1 |
|---|---|---|---|---|---|---|---|---|---|---|---|---|---|---|---|---|---|
| avg | 23.0 | 101.2 | 1.2 | 1.2 | 0.002 | 3.1 | 0.08 | 10.801 | 10.654 | 10.784 | 10.729 | 0.0532 | 0.0496 | 0.9 | 1.3 | 0.6 | 1.9 |
| std. dev |  |  |  |  |  |  |  |  |  |  |  |  |  |  |  |  |  |

Honeycrisp

| apple | QF | CN | A2 | M1 | C0 | E2 | DIA | MDT2S pre (g) | MDT2S post (g) | CPS pre (g) | CPS post (g) | JUICE (MDT2S) | JUICE (CPS) | subj. juice1 | subj. juice2 | subj. juice3 | tilt1 | tilt2 |
|---|---|---|---|---|---|---|---|---|---|---|---|---|---|---|---|---|---|---|
| 1 | 102.4 | 366.9 | 18.7 | 15.0 | 0.006 | 22.8 | 2.85 | 188.474 | 185.883 | 188.340 | 185.810 | 0.3081 | 0.3009 | 9 | 9 | 8 | 9 |
| 1 | 109.3 | 416.0 | 19.0 | 15.5 | 0.001 | 22.5 | 2.86 | 188.474 | 185.883 | 188.340 | 185.810 | 0.3081 | 0.3009 | 9 | 9 | 8 | 9 |
| 1 | 97.8 | 317.9 | 18.6 | 13.6 | 0.002 | 23.0 | 2.95 | 188.474 | 185.883 | 188.340 | 185.810 | 0.3081 | 0.3009 | 9 | 9 | 8 | 9 |
| 1 | 80.3 | 260.4 | 17.3 | 11.3 | 0.007 | 22.5 | 2.93 | 188.474 | 185.883 | 188.340 | 185.810 | 0.3081 | 0.3009 | 9 | 9 | 8 | 9 |
| 2 | 86.9 | 381.3 | 17.8 | 15.5 | 0.008 | 17.9 | 2.94 | 199.635 | 198.514 | 199.690 | 198.470 | 0.1304 | 0.1420 | 9 | 8 | 7 | 8 |
| 2 | 38.9 | 131.8 | 17.6 | 14.0 | 0.017 | 18.7 | 2.96 | 199.635 | 198.514 | 199.690 | 198.470 | 0.1304 | 0.1420 | 9 | 8 | 7 | 8 |
| 2 | 80.0 | 472.7 | 17.4 | 14.2 | 0.011 | 18.7 | 2.96 | 199.635 | 198.514 | 199.690 | 198.470 | 0.1304 | 0.1420 | 9 | 8 | 7 | 8 |
| 2 | 95.2 | 309.9 | 17.9 | 15.7 | 0.005 | 21.6 | 3.01 | 199.635 | 198.514 | 199.690 | 198.470 | 0.1304 | 0.1420 | 9 | 8 | 7 | 8 |
| 3 | 68.5 | 239.7 | 17.5 | 14.0 | 0.013 | 21.5 | 3.06 | 211.771 | 208.983 | 211.980 | 209.300 | 0.3116 | 0.3006 | 10 | 10 | 9 | 10 |
| 3 | 95.7 | 451.6 | 18.4 | 14.8 | 0.005 | 20.6 | 3.01 | 211.771 | 208.983 | 211.980 | 209.300 | 0.3116 | 0.3006 | 10 | 10 | 9 | 10 |
| 3 | 101.9 | 278.5 | 19.4 | 15.0 | 0.003 | 24.4 | 3.10 | 211.771 | 208.983 | 211.980 | 209.300 | 0.3116 | 0.3006 | 10 | 10 | 9 | 10 |
| 3 | 64.7 | 210.0 | 18.7 | 13.6 | 0.013 | 20.9 | 3.13 | 211.771 | 208.983 | 211.990 | 209.300 | 0.3116 | 0.3006 | 10 | 10 | 9 | 10 |
| 4 | 96.5 | 271.1 | 19.6 | 15.5 | 0.006 | 22.9 | 2.98 | 190.635 | 188.376 | 190.540 | 188.460 | 0.2665 | 0.2453 | 9 | 7 | 4 | 7 |
| 4 | 104.3 | 460.6 | 20.6 | 15.2 | 0.008 | 21.3 | 2.91 | 190.635 | 188.376 | 190.540 | 188.460 | 0.2665 | 0.2453 | 9 | 7 | 4 | 7 |
| 4 | 79.0 | 356.3 | 17.8 | 14.0 | 0.019 | 20.6 | 2.95 | 190.635 | 188.376 | 190.540 | 188.460 | 0.2665 | 0.2453 | 9 | 7 | 4 | 7 |
| 4 | 106.1 | 376.1 | 19.8 | 14.8 | 0.009 | 23.7 | 2.87 | 190.635 | 188.376 | 190.540 | 188.460 | 0.2665 | 0.2453 | 9 | 7 | 4 | 7 |
| 5 | 131.1 | 355.4 | 21.5 | 18.9 | 0.000 | 22.4 | 2.95 | 195.034 | 195.034 | 196.210 | 194.930 | 0.1050 | 0.1478 | 9 | 8 | 9 | 8 |
| 5 | 128.0 | 746.1 | 21.0 | 17.5 | 0.000 | 23.9 | 2.95 | 195.034 | 195.034 | 196.210 | 194.930 | 0.1050 | 0.1478 | 9 | 8 | 9 | 8 |
| 5 | 129.9 | 450.8 | 20.6 | 18.4 | 0.000 | 23.9 | 3.02 | 195.034 | 195.034 | 196.210 | 194.930 | 0.1050 | 0.1478 | 9 | 8 | 9 | 8 |
| 5 | 131.3 | 468.4 | 21.3 | 17.3 | 0.000 | 24.9 | 3.04 | 195.034 | 195.034 | 196.210 | 194.930 | 0.1050 | 0.1478 | 9 | 8 | 9 | 8 |
| 6 | 81.9 | 249.4 | 18.0 | 14.0 | 0.006 | 23.1 | 2.93 | 197.472 | 197.260 | 199.500 | 197.260 | 0.2579 | 0.2611 | 9 | 10 | 7 | 10 |
| 6 | 98.3 | 584.2 | 17.9 | 14.3 | 0.002 | 21.8 | 2.97 | 197.472 | 197.260 | 199.500 | 197.260 | 0.2579 | 0.2611 | 9 | 10 | 7 | 10 |
| 6 | 93.1 | 325.0 | 17.8 | 15.0 | 0.002 | 19.7 | 3.00 | 199.472 | 197.260 | 199.500 | 197.260 | 0.2579 | 0.2611 | 9 | 10 | 7 | 10 |
| 6 | 92.3 | 253.4 | 18.6 | 14.5 | 0.003 | 24.0 | 2.99 | 199.472 | 197.260 | 199.500 | 197.260 | 0.2579 | 0.2611 | 9 | 10 | 7 | 10 |

Figure 10F

| | | | | | | | | | | | | | | |
|---|---|---|---|---|---|---|---|---|---|---|---|---|---|---|
| 7 | 100.6 | 518.3 | 19.1 | 14.3 | 0.003 | 21.7 | 2.90 | 190.076 | 186.655 | 189.920 | 186.740 | 0.4050 | 0.3765 | 10 | 10 | 10 | 10 |
| 7 | 113.3 | 734.7 | 19.5 | 16.3 | 0.000 | 22.1 | 2.87 | 190.076 | 186.655 | 189.920 | 186.740 | 0.4050 | 0.3765 | 10 | 10 | 10 | 10 |
| 7 | 98.6 | 287.8 | 19.7 | 15.3 | 0.002 | 21.6 | 2.93 | 190.076 | 186.655 | 189.920 | 186.740 | 0.4050 | 0.3765 | 10 | 10 | 10 | 10 |
| 7 | 84.5 | 555.8 | 17.8 | 13.7 | 0.007 | 19.4 | 2.99 | 190.076 | 186.655 | 189.920 | 186.740 | 0.4050 | 0.3765 | 10 | 10 | 10 | 10 |
| 8 | 72.3 | 482.4 | 17.3 | 13.3 | 0.021 | 20.2 | 3.06 | 200.430 | 197.527 | 200.290 | 197.990 | 0.3380 | 0.2678 | 8 | 8 | 8 | 8 |
| 8 | 59.1 | 602.3 | 15.9 | 13.0 | 0.021 | 17.8 | 3.05 | 200.430 | 197.527 | 200.290 | 197.990 | 0.3380 | 0.2678 | 8 | 8 | 8 | 8 |
| 8 | 81.6 | 346.2 | 18.1 | 14.6 | 0.011 | 17.8 | 2.82 | 200.430 | 197.527 | 200.290 | 197.990 | 0.3380 | 0.2678 | 8 | 8 | 8 | 8 |
| 8 | 55.0 | 221.4 | 16.5 | 13.2 | 0.012 | 19.6 | 2.92 | 200.430 | 197.527 | 200.290 | 197.990 | 0.3380 | 0.2678 | 8 | 8 | 8 | 8 |
| 9 | 114.7 | 326.4 | 20.6 | 16.2 | 0.000 | 22.0 | 3.04 | 212.284 | 209.176 | 212.190 | 209.490 | 0.3561 | 0.3093 | 8 | 8 | 9 | 9 |
| 9 | 139.2 | 263.9 | 23.3 | 18.1 | 0.000 | 29.0 | 3.00 | 212.284 | 209.176 | 212.190 | 209.490 | 0.3561 | 0.3093 | 8 | 8 | 9 | 9 |
| 9 | 142.2 | 593.6 | 22.3 | 18.7 | 0.000 | 25.7 | 2.99 | 212.284 | 209.176 | 212.190 | 209.490 | 0.3561 | 0.3093 | 8 | 8 | 9 | 9 |
| 9 | 124.4 | 417.6 | 20.4 | 17.2 | 0.000 | 23.7 | 3.02 | 212.284 | 209.176 | 212.190 | 209.490 | 0.3561 | 0.3093 | 8 | 8 | 9 | 9 |
| avg | 96.6 | 391.8 | 19.0 | 15.2 | 0.006 | 21.9 | 2.97 | 198.747 | 196.379 | 198.741 | 196.494 | 0.2754 | 0.2613 | 9.0 | 8.8 | 7.8 | 8.8 |
| std. dev. | 23.9 | 142.2 | 1.6 | 1.6 | 0.006 | 2.3 | 0.07 | 8.242 | 8.164 | 8.300 | 8.272 | 0.0943 | 0.0736 | 0.7 | 1.0 | 1.6 | 1.0 |

AUTOMATED MACHINE AND METHOD FOR FRUIT TESTING

RELATED APPLICATIONS

This Utility patent application claims the benefit of earlier filed U.S. Provisional Patent Application No. 61/906,297 filed on Nov. 19, 2013 and titled IMPROVED AUTOMATED MACHINE AND METHOD FOR FRUIT TESTING. The entire contents of earlier filed U.S. 61/906,297 is expressly incorporated herein, in its entirety, by this reference.

U.S. 61/906,297 and all inventorship rights have been assigned by all co-inventors to Applicant Charles L. Mohr on Nov. 19, 2013. Said assignments are recorded in the USPTO at Reel/Frame 031634/0667.

BACKGROUND OF INVENTION

1. Field of Invention

This invention relates to measuring and testing, and more particularly to an improved automated fruit tester machine and method that is computer operated and uses mechanized penetration and data collection to provide measures of quality, freshness, juice content and maturation state of the tested fruit.

2. Background and Description of Prior Art

The instant automated fruit tester and method is an improvement on known fruit testing apparatus and methods including without limitation the Automated Machine and Method for Fruit Testing disclosed in U.S. Pat. No. 6,643,599 B1 issued Nov. 4, 2003 to Charles L. Mohr and Brandt C. Mohr of Richland, Wash. The entire contents, disclosure, claims and teachings of U.S. Pat. No. 6,643,599 B1 are expressly incorporated herein by this reference.

The determination of the ripeness, juiciness and the maturational state of fruit has been a human desire probably as long as fruit has been used as a food product. Through the history of such determinations the process has devolved from subjective tastable, visual and manual inspection to mechanized and sophisticated somewhat objective procedures, but substantial problems still remain to be resolved to provide meaningful objectivity. The instant invention seeks to solve or alleviate various of these remaining problems, especially as they relate to softer fruits of the pippin and drupe types.

Visual inspection and manual manipulation are only rudimentary indicators of ripeness and not indicative to any substantial degree, if at all, of maturational state, both by reason of their substantial subjectivity and their lack of any substantial functional relationship to the characteristic sought to be determined. Both methods are still widely used not only by unsophisticated consumers, but also by professionals.

In the early development of more objective fruit testing, the firmness of fruit, or more properly its resistance to pressure deformation or plunger penetration, were found to be more reliable indicators of ripeness and maturation state than visual appearance, manual manipulation and other similar subjective determiners. In modern fruit testing, measures of firmness are more widely used as indicators of the fruit condition than are more subjective attributes. As the desire for increased accuracy of fruit testing grew, the testing processes passed from the partially subjective manually manipulable penetration processes to the greater objectivity of mechanically controlled testing devices, firstly of the manually operated type and subsequently of the mechanically powered and controlled type, to increase accuracy, reliability and repeatability of the testing results. Mechanical testers have developed along the lines of both destructive or penetration type devices and nondestructive or impingement type devices, with representatives of each type of device being used in the modern day fruit testing arts.

Probably the most commonly used present day fruit tester, and that which often serves as the determiner of fruit quality for regulatory agencies, is a manually operated intrusion type tester that provides a cylindrical plunger which is inserted by direct manually applied force into the meat of a fruit to an often variable depth by an operator with measurement of only the maximum force required for insertion being determined and used as the indicator of fruit quality. Such testers provide quite variant results when determined by repeatability, are fairly unreliable in determining fruit ripeness and are substantially unreliable in determining the state of fruit maturation, which is indicative of the course of future development and especially of shelf life of the fruit. Such testers do not measure or attempt to measure juice content of the fruit. The modern trend in private, as opposed to regulatory, testing devices has been toward more sophisticated non-destructive impingement type devices that measure force required for impingement of an object into a fruit surface without skin rupture or the amount of impingement caused by a predetermined force applied on the surface of the fruit by an object or a pressurized gas stream.

The instant mechanism differs from this current and other known fruit testing apparatus by providing a computer controlled intrusive plunger that is mechanically forced into a fruit to a substantial predetermined depth at constant velocity, constant load or a combination of both for measurement in rapid sequence of the mechanical resistance to plunger penetration throughout the length of the plunger's intrusive course. The mechanism provides an electrically powered motor that drives a ball-screw motion translator through a transmission mechanism. The motor has an attached encoder and associated control circuit that regulate the velocity and rotational direction of the motor and thereby the linear velocity and displacement of the plunger responsive to software generated computer commands. The plunger is supported through a load cell which measures the force applied to the plunger throughout its trajectories. The plunger displacement, velocity and applied force measurements are communicated to an associated computer by feedback circuits for recordation and analysis at approximately 30,000 sequential sampling points along a single plunger trajectory.

Prior testers that have provided intrusive plunger type testing of fruit or similar penetrable products generally have not provided for the accurate determination of force resisting plunger penetration at closely spaced and positionally determinable points along a predetermined plunger trajectory and are distinguished from the instant mechanism in this regard. Additionally prior devices are not known to have allowed the selective determination of resistive force of a fruit to plunger penetration at either constant velocity or constant load, to have provided sufficient accuracy in control and measure of plunger speed and position to provide consistently repeatable results and have not determined penetration resistance at such small increments as is allowed by the instant device. Further still, prior devices have not determined or measured the juice content of the fruit being tested and used the measure of juice content as an indicator of fruit maturity and quality.

The accuracy of control and measurement of the instant tester arises from the computer controlled and electronically sensed mechanical structure that provides a motor powering a speed reducing cog belt transmission that operates a ball screw motion translator to lineally move a plunger interconnected through an intervening strain gauge block having four strain gauges interconnected in an amplified bridge circuit for force measurement and a precision scale to measure changes in weight of the fruit before and after testing to determine the juice content of the fruit. This type of finely controllable and accurately determinable system and scale is not known to have been previously used for penetration type fruit testing purposes.

The development of such a precision tester has given new insight not only into existing fruit condition, but also into the state and theory of the fruit maturation process itself which has allowed development of new methods for determining ripeness, life stage, condition and future development as a function of time. The instant tester and method thusly provides both a scientific informational tool and a practical economic tool to aid determination of conduct for dealing with fruit, both before and after picking. It has been found by accurate and fine measurement at closely placed intervals along a fruit radius that resistance to plunger penetration varies considerably in different parts of a fruit and that this variance is more functionally related to the physiological state of the fruit, and especially to maturation, than is an average or maximum measure of resistivity to plunger penetration.

This functional relationship and various of its patternations and their relationships to each other have been used to develop new and different measures of fruit maturation and to give new insight into the nature of that process to allow it to be more meaningfully and accurately used in dealing with fruit throughout the various developmental stages of its life span.

The peripheral zone of most fruits, and especially of apples, generally provides less resistance to plunger penetration than the radially medial or central core area in any state of fruit maturation, prescinding from the initial force required to penetrate the fruit skin.

With the finer analysis allowed by the instant tester and method it has been found that the physical characteristics commonly associated with fruit ripeness and quality vary considerably in different radial zones of the fruit at any given time, with characteristics commonly associated with ripeness and with subsequent deterioration occurring at different rates in different radial zones of the fruit, so measurement of firmness in the outer layer is a poor predictor of internal fruit condition. This finding has allowed measurements of characteristics in different radial zones of a fruit to both accurately determine the existing state of the fruit and also serve as an accurate means of predicting the change in the nature of the fruit at future times. This has allowed development of methods and processes for use with the instant tester and method that provide accurate prediction of ripeness, which heretofore often has been related to the balance of starch and sugar content, and of subsequent consumer desirability, which largely has been related to crispness or firmness of the fruit meat and the juice content of the fruit mean especially in the outer peripheral zone. The instant tester and method also allows accurate predictability of acceptable limits for these conditions and determination of the time when the limits will be attained to make the fruit unacceptable.

Processes have been developed and are presented for establishing numerical determination and determination of limits for fruit quality from combined measures of parameters derived from data developed through an entire fruit radius, especially to determine the desirability or quality of the fruit at the time of measurement. Comparative processes have also been developed and are presented to use the data within different radial zones of a fruit to not only provide accurate numerical indicators of quality, but also to relate the parameters in the different zones to each other to provide accurate indicators of the state of fruit maturation and a reliable method of predicting the future state of maturation of the fruit at future times. The measurement of parameters may be continuous through the entire fruit radius or more simply may be based on measures in three logically distinguishable zones of a fruit comprising and outer peripheral zone adjacent the fruit skin, a medial meat zone and the central core zone, or may be otherwise differentiated and refined to provide more detailed and accurate measures for particular types of fruit and particular conditions to be determined. These processes are distinguished essentially from maximal, minimal or gross averaging processes for determining fruit characteristics without regard to the area where the determined parameters are present. The analyses presented generally have not been possible with prior testing apparatus which did not provide sufficient reliability or fineness to allow repeatability of the tests to any substantial degree and have not heretofore been used in commercial or regulatory testing.

As seen in FIG. 6, a fruit defines a first outer radial zone denominated R-1 that extends from the peripheral skin to an arbitrary average depth of approximately 0.320 inch. This depth is determined as the depth normally tested by manual pressure testers of the present day and establishes a basis for determining some relationship between the instant testers and historical testers. A second medial radial zone denominated R-2 comprises the meat region of the fruit where most of the edible portion of the fruit resides. This R-2 zone extends from the R-1 zone inwardly a spaced distance to an innermost R-3 zone. The inner core region of the fruit is designated as the R-3 zone and in general is substantially proportional to the fruit radius. The texture and quality and juiciness of a food item (for purposes of this patent disclosure an apple) is best represented quantitatively by a Quality Factor (QF), which is a weighted sum of the results of rigorous materials test routines. The QF is scaled between 0, representing Washington State Apple Commission minimum shipping requirements, and 100, representing the Apple Maturity Program's optimum picking guidelines.

The premise underlying the development of the QF is that the majority of the edible portion of the fruit should be included in any assessment of fruit maturity. Further, to make the measurement reliable and consistently accurate, the results of several independent types of tests should be combined. By comparison, present the industry-standard Magness-Taylor style penetrometer test measures only the maximum force in the outer 0.32 inches of a fruit.

The following measurements are components of the Quality Factor (QF) determination:

M1=Maximum force in region R1, defined by the region of the apple from the surface to 0.32 inches in depth. This test is performed at a computer-controlled constant velocity.

C0=Creep deformation is defined as fruit meant displacement and is obtained through application of a constant force and movement of the plunger to keep the force constant as the apple material relaxes. The C0 measurement is made when the plunger first reaches a depth of R1. At this depth, the computer control switches from constant velocity testing to a constant load mode of operation, targets a constant plunger force specified in software, and maintains that load for the period of time specified in software. This is usually 0.5 seconds to a maximum of 2.5 seconds with a force of 10 pounds for apples. As an apple ages and breaks down due to the maturation process, the C0 deformation will increase significantly.

A2=Average Firmness in Region 2. After the creep test is completed, the test is resumed with the same constant velocity trajectory used for the initial part of the test. The force readings obtained from moving the plunger from R1 to R2 are averaged and the average firmness in R 2 is used as one of the parameters to characterize the fruit quality. In a fresh apple, A2 will be several pounds higher than M1.

E2=Average of the Last 20 Firmness Readings in Region 2. The value of E2 in a crisp apple will be greater than both M1 and A2. As the maturation process of the fruit continues, the values of A2 and E2 drop significantly. The E2 measurement is preferably made over the last 0.01907 inches of plunger travel, starting with 200 raw samples taken at 5000 Hz over 0.040 sec then down sampled to 20 readings. The plunger velocity is preferably 0.4768 inches/sec.

CN=Crispness Measurement. This measurement is in essence a quantification of the "crunch" that would be obtained when biting the fruit. The crispness measurement is made in the mid-region of the fruit during the constant velocity portion of the test as the plunger moves between R1 and R2. It is based on the 5000 Hz sampled force data that is treated to allow a Fourier Transform of the deviation from a least-squares cubic spline calculated as the best fit of the force data. This relatively high frequency change in force transmitted to the load cell by the plunger as it passes through the mid-region of the fruit is a good measure of the fruit crispness, or tearing characteristics.

QF=Quality Factor. The five individual terms: M1, CO, A2, E2 and CN are combined into a single term called the Quality Factor (QF). The method for developing the QF is as follows. Apples from the database used for development that fit the criteria are sorted; those with the highest readings are given a scale value of 100 for each of the measurement categories. The value of zero is determined by recording the lowest values for each of the five terms that are found in apples nearing unacceptable maturity levels and which have poor texture. Linear correlations have been developed for each of the five terms that allow the measurements from the apple being tested to be converted into individual QF (Scale) terms of 0 to 100. The QF (Scale) terms are summed for the five values and averaged to give the overall Quality Factor (QF).

The Quality Factor is a weighted sum of the five tests, and is designed to provide an easily-interpreted measure of consumer acceptability. Scaled between 0 and 100, the QF identifies fruit that is reaching optimal picking maturity (QF=100) or falling below the pre-shipping acceptability limit (QF=0).

The QF determination is used industry wide and the five terms (measurements) have been widely adopted and accepted to characterize overall fruit quality and storability for time of picking and for storage potential assessment. The instant improved testing apparatus and method provides an even more accurate and thorough test of overall fruit quality by adding a measure of the fruit's juice content to the known five measurement parameters. Inclusion of the fruit's juice content in an assessment of the taste and texture related factors increases and improves the accuracy and usefulness of overall fruit quality assessment.

Apples and other fruits and vegetables (collectively, "produce") contain water and soluble solids known as juice. The apple is used as a example fruit in this disclosure, however the principles described herein apply to other types of produce as well.

Juiciness is an important textural attribute and of primary interest to the consumer as well as the produce retailer because it is something that the consumer can taste and base their purchasing decisions upon. Juiciness is typically expressed in qualitative or semi-quantitative terms as graded by a human taste-tester. Heretofore no accepted technique has previously been described to measure or otherwise quantify juiciness in an automated fashion.

Although the overall juice density (or juice content) of the produce (as measured by measuring the weight loss of a sample of known volume before and after oven drying) may be of interest to characterize the hydration state of the produce, this quantity does not necessarily correlate with the sensory textural attribute described as juiciness. Other important sensory textural attributes include firmness, crispness, and mealiness, among others.

$$\text{Juice Density}=(\text{weight before oven drying}-\text{weight after oven drying})/\text{volume}$$

The instant improved automated machine and method for fruit testing allows for automatic measurement of changes in weight of a fruit, (an apple) from before the test series is performed and then to retest the apple weight after the test series have been completed on each apple. The customary operation is to perform at a minimum two penetration tests on a given apple. The "sun side" of the apple and the "shade side" are the usual test points since the maturity of the apples is significantly affected by the sun exposure. Additional tests on 90 degree positions (from the "sun side" and from the "shade side") are also possible. These measurements can be summed to one apple with multiple test points and then averaged for that fruit.

Specific Juice Content (SJC) can be thought of as the density of expressed (or expressible) juice per unit displaced volume of fruit. Thus while the fruit contains a certain amount of juice overall (juice density), only a fraction of this is available as free juice capable of producing the sensory attribute of juiciness. SJC quantifies this free juice.

The instant inventive apparatus and method is a recognition that juice expressed from the fruit during a penetration test is an indicator of the general juice content in the fruit. It was further recognized however that the juice content per unit volume of the fruit may be greater than the measured difference determined by the difference in weight (before and after), and testing has shown that the measured difference is an indicator and proportional to the actual Specific Juice Content (SJC) of the fruit.

The Specific Juice Content is defined as the total change in weight of the fruit divided by the sum of the total plunger travel distance in each of the test sites. The volume of the plunger is a known for the calculation. SJC is measured as units of grams/cubic centimeters. (G/cc).

Test data generated from a number of samples from fresh apples to older apples shows the relationship between SJC and the other five Quality Factor (QF) terms disclosed in U.S. Pat. No. 643,599. In the instant invention SJC is included in the QF calculation and may be weighted more than the other QF terms because of the impact on the sensory perception of fruit quality for eating.

Testing has been performed to characterize SJC in relation to other sensory textural characteristics. A representative series of tests using Braeburn apples (FIGS. 7, 8, 9), are generalizable to other varieties of apples and other types of produce.

The instant inventive apparatus and method allows an SJC measurement to be made by measuring the distance traveled into the fruit body and the distance relative to the surface and the core boundary of the apple and can keep track of the total distance traveled for multiple tests on the same fruit sample.

The inclusion of the SJC measurement with the other known testing parameters increases the breadth of the Quality Factor (QF) in addressing fruit eating desirability.

SJC is a new measurement produced by the instant invention designed to quantify the juiciness of apples and other produce. SJC represents the density of free juice per unit displaced fruit available to contribute to the sensory attribute of juiciness, which is typically expressed in qualitative or semi-quantitative terms by human taste-testers. SJC as measured by the instant invention can be used to express juiciness quantitatively, helping to augment or replace laborious and subjective human taste-testing.

The instant invention resides not in any one of these features individually, but rather in the synergistic combination of all of the structures of the tester and method which necessarily give rise to the functions flowing therefrom and the analysis processes essentially related thereto, as herein specified and claimed.

SUMMARY OF THE INVENTION

An improved fruit tester and method provides a plunger intrusion-type mechanism, a precision scale and an associated computer for control of the mechanism and for recordation, presentation and analysis of data sensed by the mechanism. An electrically powered variable speed motor carries an optical encoder to sense rotary direction and speed data, which is transmitted through circuitry to the associated computer for analysis to determine control data to maintain pre-programmed motor function. Computer software determines plunger position and resultant penetration into a fruit at either pre-determined plunger speed or constant plunger resistive pressure in fine increments at least as small as one in 32,000 parts over the plunger trajectory and stores this data in computer memory. The precision scale is used to determine the weight of the fruit before and after the penetration tests and the difference in weight is used to automatically calculate the Specific Juice Content (SJC) of the fruit.

Processes allowed by the fine measurement of parameters are set forth to determine and numerically represent the Specific Juice Content, maturation state and present condition of fruit, generally of either pippin or drupe types, by analyzing the data through a radius of the fruit or in radial zones. Processes are also set forth for numerically determining and predicting the future maturation state of the fruit at future times by comparing the functional relationships of parameters within different radial zones.

In providing such an improved fruit tester and method it is:

a principle object to determine the Specific Juice Content of a food item relative to the food item's volume.

a further object to include Specific juice Content of a food item to the evaluation of the quality, maturation state, taste and consumer appeal of a food item.

a further object to provide a plunger type intrusive tester that is serviced by a computer to allow measurement of plunger position at least 30,000 data points in a radial trajectory into a fruit and resistance to plunger penetration with a accuracy of at least 0.001 pound over a radial trajectory extending from the periphery to the center of the core area of a pippin or to the stone of a drupe.

a further object to provide such an intrusive tester that has a mechanism controlled by computer output data determined from mechanism input data with all data transferred between the mechanism and computer through circuitry.

a further object to provide such a tester that is of relatively small and portable nature and may be battery powered for field testing.

a further object to add Specific Juice Content (SJC) as an additional component of the industry recognized Quality Factor (QF) measure.

a further object is to provide such a tester that measures resistance to plunger penetration both at constant plunger velocity and at constant force resisting plunger penetration.

a still further object is to provide such apparatus and processes for measurement and determination of fruit condition that may simulate the results of present day manual impingement testing, but with substantially greater accuracy and repeatability.

a still further object is to provide such apparatus and processes that measure resistance to plunger penetration in predetermined radial zones of a fruit to allow comparison of the parameters in different zones to provide an accurate indicator of the present state and maturity of the fruit, methods for estimating fruit condition at future times, methods to estimate the time of ripeness of immature fruit for picking and the commercially acceptable life span of mature fruit.

a still further object is to provide such a tester that is of new and novel design, of rugged and durable nature, of simple and economic manufacture and one that provides accurate and repeatable test results with various fruits, vegetables or similar materials that are tested by plunger penetration and to provide essentially related processes for the determination of present condition, maturation state, future development and consumer desirability as allowed by reason of the fine, accurate and detailed data provided by the tester.

Other and further objects of the invention will appear from the following specification and accompanying drawings which form a part hereof. In carrying out the objects of the invention, however, it is to be remembered that its features are susceptible of change in design and configuration with only one preferred embodiment of the best known mode being illustrated and specified as required.

BRIEF DESCRIPTION OF THE DRAWINGS

In the accompanying drawings which form a part hereof and wherein like numbers of reference refer to similar parts throughout:

FIG. 1 is an isometric view of the fruit tester interconnected an associated lap-top computer and a precision scale.

FIG. 2 is an enlarged isometric view of the tester of FIG. 1 with case removed to show various parts, their configuration and relationship.

FIG. 3 is an enlarged isometric view of the tester of FIG. 2 rotated ninety degrees in a counterclockwise direction to show various additional components and internal structure.

FIG. 4 is an enlarged partial vertical cross-sectional view through the upper portion of the tester of FIG. 3, taken on the line 4-4 thereon in the direction indicated by the arrows, to show details of the powering train and supporting top frame.

FIG. 6 is an idealized diagram pippin type fruit showing the three logical zones of a pippin type fruit used for data analysis.

FIG. 7 is a graph of three lots of Braeburn™ apples acquired from different sources (retail and wholesale and fruit packer) showing the relationship between Specific Juice Content as a fraction of total juice density indicating firmer fruit expresses more juice.

FIG. 10 is a compilation of test data results for various types of apples tested showing the individual QF measurements, the weight of expressed juice, the subjective TILT scores from the two taste testers and the relationship between QF scores and Specific Juice Content.

DESCRIPTION OF PREFERRED EMBODIMENT

Figure 5:
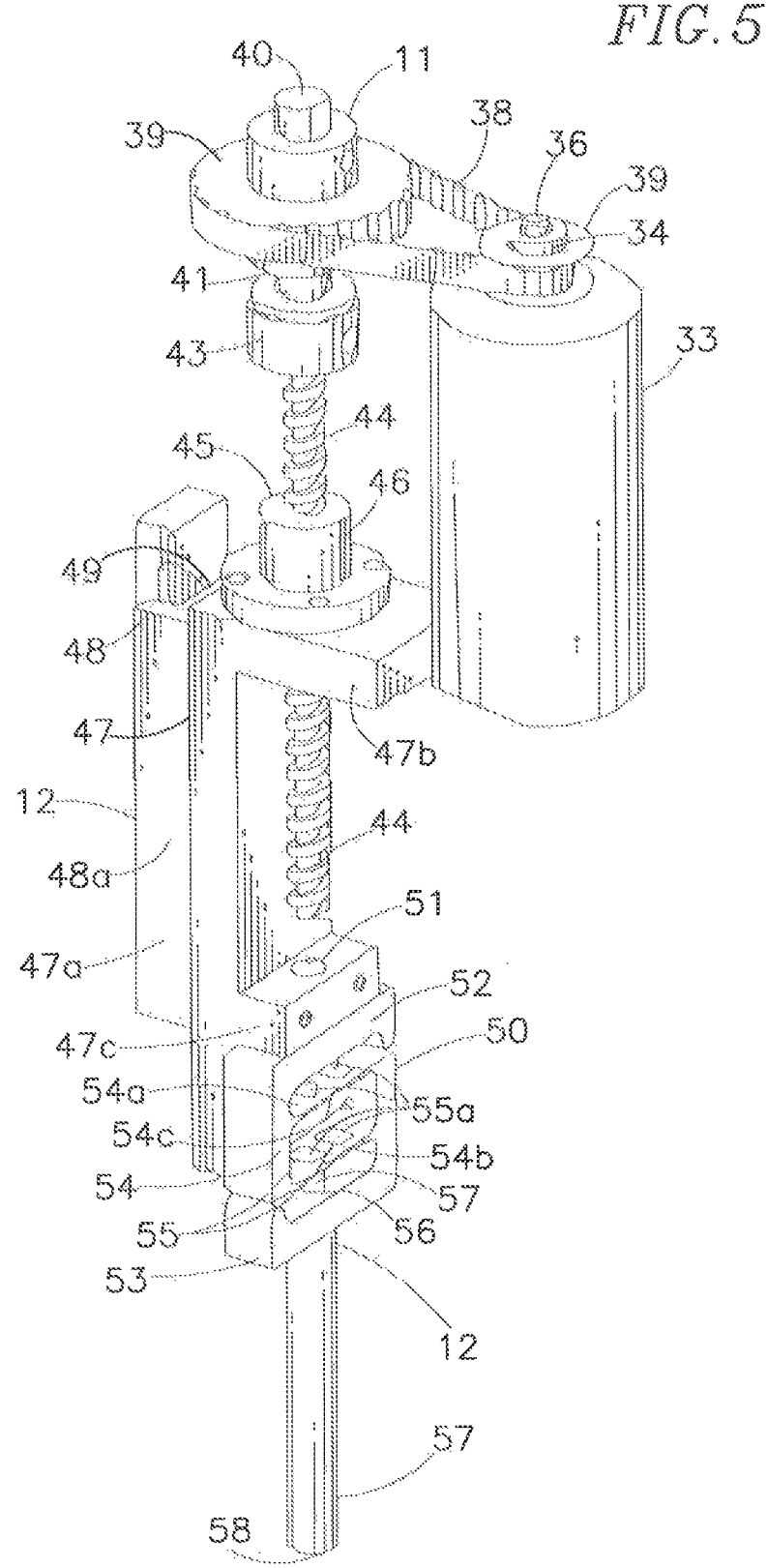
FIG. 5 is an isometric view of the powering train and plunger structure of the tester of FIG. 2 isolated from the tester to better show the various parts and their relationship.

The instant fruit tester generally comprises frame 9 enclosing testing chamber 10 in its lower portion and carrying powering train 11 to move plunger structure 12 within the testing chamber 10 to operatively engage fruit 76 positioned within the testing chamber 10. Control member 13 carried by the frame 9 receives software generated control data from associated computer 14 to operate the powering train and senses, receives and transmits process data to the computer 14 for analysis, displays and recordation. A precision scale 100 communicating with the computer 14 and control member 13 determines weight of the fruit 76 before testing and a weight of the fruit 76 after testing to provide measures for determining Specific Juice Content (SJC).

Frame 9 provides rectilinear base 15 supporting elongate upwardly extending left side 16 and peripherally similar right side 17 in parallel lateral alignment on the elongately medial portion of the base. Top 18 is structurally carried between the upper portions of the right and left sides 16 and 17 respectively. Back plate 19 is carried on rearward facing edges of the sides 16, 17 in their medially upper portions. Forward circuitry support panel 20 is carried on forward edges of sides 16, 17 in their medially upper portions. These frame elements are all structurally joined at their adjacent portions by fasteners 21.

Upper surface of base 15 carries centering plate 23 between sides 16, 17. The centering plate 23 is a circular disk with upper surface 24 configured to define a shallow depression formed as an inverted cone having its apex aligned with the axis of the centering plate 23 and defining a central angle between diametrically opposed ruling lines of 160 degrees to support fruit 76 and maintain the fruit 76 in a somewhat centered position by reason of the curvilinear configuration of the fruit 76, regardless of its orientation. The centering plate 23 is structurally positioned and maintained on the base 15 by threaded fasteners (not shown). Stripper plate 25 is carried between sides 16, 17 spacedly above the centering plate 23 at a distance that allows fruit 76 to be tested to be inserted between the stripper plate 25 and centering plate 23. The stripper plate 25 defines medial hole 26 incrementally larger than a plunger 57 to be used in the tester so that the plunger 57 may extend through hole 26 for unencumbered motion to penetrate a fruit 76, but yet the stripper plate 25 will prevent motion of the fruit 76 upwardly past the stripper plate 25 when the plunger 57 is extracted from the fruit 57.

Testing chamber 10 is defined in the lower portion of the frame between base 15, sides 16 and 17 and stripper plate 25 spacedly thereabove. The rearward portion of the testing chamber 10 is enclosed by rear shield 27 having body 27a configured as a semicircular sector of a cylinder with laterally extending coplanar legs 27b extending outwardly from each side edge to fit in adjacency on the lower portions of the rearward facing edges of frame sides 16, 17 where they are positionally maintained by fasteners 28. The upper surface of rearward shield 27 structurally carries top cover 29 to prevent entry of downwardly moving debris into the rearward part of the testing chamber 10. Front shield 30 is of a configuration similar to the rearward shield, but preferably has no top cover. One front shield leg 30b carries spaced hinges 31 which are supported by left frame side 16 to allow pivotal motion of the front shield to open for access to the testing chamber 10. The hinges 31 preferably are of a biased type to provide a null closure mode for the door. A catch (not shown) may be provided to maintain closure if desired. Preferably the front shield body 30a extends spacedly forwardly of the forward portion of peripheral cover 22 so that the forwardly projecting shield portion may be used for manual grasping to aid opening and closing manipulations of the front shield 30.

As seen in FIGS. 2, 3 and 4 upper motor support plate 32 is carried on the upper surface of top 18 to mount depending motor 33 in motor orifice 34 defined in top 18 and there positionally maintain the motor by bolts 35 extending between the motor support plate 32 and the motor casement. Motor drive shaft 36 irrotatably carries cog belt pulley 37 that drives endless cog belt 38 extending rearwardly to operatively communicate about driven belt pulley cog 39 irrotatably carried by screw drive shaft 40. The screw drive shaft 40 is carried in thrust bearing 41 carried in top 18 and positionally maintained against downward motion by bearing plate 42 supported on the undersurface of top 18 by bolts 42a. The lower end of screw drive shaft 40 defines radially larger collar 43 having medial orifice 43a to receive and irrotatably interconnect the upper end portion of screw shaft 44 by means of bolt 44a.

As seen in FIG. 5 the screw shaft 44 of ball-screw motion translator 45 depends spacedly below its interconnection with collar 43 to operatively interconnect translator body 46. The ball-screw translator 45 converts rotary motion of the screw drive shaft 40 into linear motion of the translator body 46 to responsively move plunger structure 12 in a vertical direction. Such ball-screw motion translators have been long known in the mechanical arts and therefore are not described in detail.

The ball-screw translator body 46 is structurally carried by plunger slide 47 depending therefrom. The plunger slide 47 provides vertically elongate rectilinear body 47a having perpendicular forwardly extending horizontal upper leg 47b and lower leg 47c. The translator body 46 is structurally carried on the upper surface of the upper leg 47b and that leg 47b defines an appropriately configured and positioned hole to allow the lower portion of the screw shaft 44 to depend therethrough for vertical motion of the plunger slide 47 on the screw shaft. The distance between the upper leg 47b and lower leg 47c is such as to allow sufficient vertical plunger motion for penetration through at least the upper radius of a fruit 76 to be tested. The slide body 47a carries rearwardly extending, vertically elongate slide rail follower 48 having similar spaced rearwardly extending legs 48a that slidably receive and positionally maintain slide rail 49 therebetween. The slide rail 49 is structurally carried by back 19 of the frame 9 as shown in FIG. 3.

Plunger slide lower leg 47c carries stress block 50, by means of threaded fastener 51 extending therebetween, depending from the lower surface of the lower leg 47c. The stress block is of an "S" type providing similar cantilevered upper leg 52 and lower leg 53 each having laterally opposed vertically extending portions that are interconnected by medial laterally extending body 54 defining a rectilinear orifice 54c to separating cross-sectional smaller upper arm 54a and lower arm 54b of the beam for stress measurement. Laterally medial portions of the upper and lower beam arms 54a, 54b carry spaced strain gauges 55 to measure force imposed between the upper and lower legs 52, 53 of the stress block 50.

Lower leg 53 of the stress block 50 defines medial threaded hole 56 to receive the threaded upper portion of plunger 57 in vertically adjustable interconnection. The plunger shaft 57 depends from the stress block 50 a spaced distance to allow its penetration to at least the medial portion of fruit 76 to be tested when carried by the centering plate 23. The lower end portion 58 of plunger shaft 57 may be variously configured for particular purposes, but for ordinary testing it is preferred that the plunger end be configured as a segment of a sphere having a radius somewhat greater than the radius of the plunger shaft, though other plunger end shapes are within the ambit and scope of our invention, but may produce somewhat different test results.

Preferably for ease of operation, analysis and accuracy of the entire drive train and plunger assembly are so configured and related that drive shaft 40 and plunger shaft 57 are coaxial on a line that is coincident with the axis of centering plate 23 to allow the plunger 57 to penetrate substantially vertically into a tested fruit 76 to create substantially vertically oriented resistive forces to plunger penetration and eliminate substantially all laterally directed force components. The spherical configuration of plunger end 58 and the fruit's support on the centering plate 23 also combine to eliminate or reduce non-vertical plunger 57 penetration and laterally directed forces caused thereby. The maintenance of vertical radially orientated plunger penetration aids in preventing erroneous, irregular and non-repeatable results in fruit testing.

Control member 13 provides two sided circuit board 59 mounted between the vertically medial portions of sides 16, 17 of frame 9, between motor 33 and the adjacent depending portion of powering train 11. The circuit board 59 communicates with adjacent perpendicular elongately extending control panel 60 that is externally accessible through peripheral cover 22. The control panel 60 provides a mounting area for electrical connection fixtures and controls that may require frequent access.

The primary power source for the tester is rechargeable battery (not shown). The battery (not shown) communicates through a state meter and power switch, both carried on control panel 60, to provide power for the control member 13. An external battery charger (not shown) may be used to charge the battery from an external 120 volt AC power source.

A motion controller 68 is a special purpose digital processor with embedded software to provide control signals required to cause motor 33 to move through a predefined sequence of motions to move plunger 57 through a predefined testing program herein termed a "trajectory". The trajectory command sequence consists of several data bites to define motor operating mode, position, speed and acceleration. The movement of motor drive shaft 36 is sensed by an optoelectronic shaft encoder. (not shown). The actual operating parameters of the motor 33 are compared with computer software commanded values. Command signals are responsively communicated from the computer 14 and command interface to the motion controller 68.

A communication port of computer 14 is used to pass digital information in both directions between computer 14 and the control member 13 and the precision scale 100. Control instructions are sent from the computer 14 to the control member 13 circuits and measurement data of pressure, plunger position, weight of the fruit, SJC calculation and operational status is returned to the computer 14.

The operation of our tester may be understood from the foregoing description of its structures and functions.

A tester and precision scale 100 formed as specified is attached by a communication cable to associated computer 14. The tester is powered by a battery and its operation after institution is controlled by software carried by computer 14. The fruit 76 to be tested, in the instance illustrated an apple, is first placed on the scale 100 and the scale 100 is allowed to settle to accurately determine the weight of the fruit 76. The weight of the fruit 76 is recorded and maintained in the computer 14 memory. The fruit 76 is then removed from the scale 100 and placed in testing chamber 10 to rest upon centering plate 23 and the testing chamber front shield 30 is closed to operate switch 72 to allow power to pass to motor 33. The computer software is adjusted to desired parameters for the particular type of test, plunger trajectory and plunger speed and the tests are then instituted by the software upon command.

In the preferred embodiment of the tester for apples, encoder 69 distinguishes 1024 data points per motor shaft rotation and corrects motor velocity to within two encoder points for each 256 point sampling interval. The rotary motion of the motor shaft is transmitted from motor 33 through the cog-belt 38 with a 4:1 speed reduction to ball screw translator 45 which has a pitch of 0.125 inch. This mechanical arrangement provides potential sensitivity of 32,768 data points per inch of plunger travel. The force resisting plunger 57 motion is measured by the stress block 50 which has a stiffness of approximately 550 pounds per inch of motion with a measurable sensitivity of at least 0.25 ounce (0.016 pound).

Upon test institution responsive to computer command, the motor 33 first advances the plunger 57 at higher speed to the surface of a fruit 76 to be tested. The fruit 76 surface is detected by the increase in force resisting plunger 57 motion as sensed and indicated by the strain gauge 55. At this point responsive to the sensed force the plunger motion is set to the predetermined velocity for testing the fruit 76. The diameter of the fruit is computed from the upper surface position with reference to the known centering plate 23 position and the plunger trajectory data and computed fruit center location is sent to the motion controller 68. Having the diameter of the fruit 76 calculated allows the computer to determine the volume of the fruit 76 using known geometric formulas.

The fruit 76 is tested at each selected interval of plunger displacement and the force resisting plunger 57 penetration is checked for each interval and read as preselected by the software. When the center of the fruit 76 is reached by the plunger 57, the plunger 57 is withdrawn at a higher speed as selected by the software, the test data may be visually displayed on the associated computer display screen and recorded in the computer memory. The fruit 76 is removed from the test chamber 10 and again placed on the scale 100 whereupon the weight of the fruit 76 after the test is determined and recorded in the computer 14 memory. The weight of the fruit 76 determined prior to the test is compared against the weight of the fruit 76 after the test and the change in the weight is used to calculate the Specific juice Content (SJC) of the fruit 76, and the tester is reset for another test.

This testing overcomes various of the deficiencies of common manually operated tests that are presently employed in the fruit industry by growers, processors, merchandisers and inspectors. The current manual testing method uses an apparatus that measures the maximum resistive force obtained by inserting a plunger, usually of 0.440 inch diameter for apples and 0.31 inch diameter for pears, into a fruit to a depth of approximately 0.3 inch. This manual testing method provides a simple concept but does not provide means for regulating plunger speed as the plunger penetrates into the fruit, and that penetration speed varies widely with different operators and in different portions of the fruit to provide quite variable results. This variability is caused largely by the variance in the viscoelastic properties of the fruit tissue in general and especially in different radial zones of a fruit, as fruit tissue generally will not statically support a plunger under fixed load without displacement. The fruit tissue will creep away from the plunger to relax the resistive load, so the faster the plunger is moved the higher is the load resisting plunger motion and conversely the slower the plunger is moved the lower is the load resisting motion. The differences between this presently standard testing method and that allowed by the instant improved tester and method provide substantial information concerning the nature of fruit maturation which in turn has given rise to new and novel testing methods and results which were not heretofore possible with the manually operated intrusive type tester, or in fact with other known impingement testers.

The instant tester in forcing a plunger 57 into a fruit 76 allows plunger 57 penetration at a predetermined constant velocity or at a predetermined constant load and measures the resistance to plunger 57 penetration rapidly and at closely spaced data points throughout the plunger 57 trajectory. In discussing the tester operation herein the term "pressure" is used to indicate the force resisting plunger 57 penetration into a fruit 76 as this term is commonly used in the industry, though the term may not be literally correct as the pressure is functionally related to the configuration of a particular plunger 57. Most plunger 57 sizes and shapes however, are fairly standardized to make the term reasonably accurate. The instant tester allows measure of resistive pressure with an accuracy of approximately 0.0156 pound and allows data sampling on a time frequency of preferably at least 5000 cycles per second, both with substantial accuracy and repeatability of results. This measurement process has given new detailed insight into the nature of the existing state of a fruit and also of its maturation state and process.

As a fruit matures, and especially an apple, whether on a tree or separated therefrom, the ongoing metabolism causes the internal structure of the fruit to change as a function of time to responsively cause lower pressure resisting the penetration of a tester plunger. This process is not uniform over the entire fruit mass and especially in different radial zones of the fruit. The change in internal structure continues with time, as a fairly direct function of the metabolic process, to eventually result in a fruit that is commercially undesirable. Various historical and handling parameters influence the rate and extent of the metabolic process such as growth history, varietal nature, picking time, storage temperatures and atmosphere, ethylene gas storage processes and especially time of removal therefrom and other similar conditions can have significant effect on the maturation process.

Unfortunately current fruit testing practices do not adequately show the fine and subtle changes in fruit to accurately determine its state of maturity during and after the growing season and the historically traditional indicators of fruit state such as texture, color, starch and sugar levels are not sufficiently accurate to determine either the present state of the fruit or predict its future development. It has been found with the instant tester and testing processes that in general fruit maturation develops somewhat similarly but sequentially within each of three definable zones of a fruit, though the maturation may vary substantially between those zones at a given time. The zones do not have clearly determinable and definite boundaries and boundaries must generally be determined in individual cases and with particular types and species of fruit, but the relationship of the sequence of maturity in the three zones maintains its essential nature.

As seen in FIG. 6, a fruit defines a first outer radial zone denominated R-1 that extends from the peripheral skin to an arbitrary average depth of approximately 0.320 inch. This depth is determined as the depth normally tested by manual pressure testers of the present day and establishes a basis for determining some relationship between the instant tester and historical testers. A second medial radial zone denominated R-2 comprises the meat region of the fruit where most of the edible portion of the fruit resides. This R-2 zone extends from the R-1 zone inwardly a spaced distance to an innermost R-3 zone. The inner core region of the fruit is designated as the R-3 zone and in general is substantially proportional to the fruit radius. To simplify analysis of data and allow it to be more easily and fully dealt within the instant process, the data has been classified into these three zones, but it must be realized that the only boundaries that have physical definition are the periphery of the fruit or outer surface of the R-1 zone and the core portion or outer surface of the R-3 zone, with the division between the R-1 and R-2 zones having no particular physical determinant but rather being arbitrarily determined.

Manual pressure testing is widely variant in repeatability tests not only because of variations between individual tester manipulators based largely on the velocity of insertion of a plunger to differing depths and determining only a maximum pressure reading, but also because the testing method commonly samples substantially only the R-1 zone of a fruit, and under present standards and practices makes no determination in any substantial portion of the fruit's condition of the R-2 or of R-3 zones. Testing with the instant tester has suggested that fruit pressure can remain relatively constant in the R-1 zone while internal fruit pressure, and therefore texture, crispness, and juice content can continue to decline in zones R-2 and R-3 to provide an erroneous determination not only of the existing state of the tested fruit, but also erroneous indication of its maturation state and consequently inaccurate prediction of its condition at future times. Testing has also indicated that the rate of change in fruit pressure in zone R-1 is slower than in the interior zones R-2 and R-3 which change at a more rapid rate to exacerbate the problem.

The measurement of creep, or the fruit meat displacement occurring at a constant plunger pressure, is especially related to apple maturity and adds a new dimension to test data. Certain apple varieties such as the Fuji, are structurally robust enough to be held for long periods on a tree to produce water-core that may be desirable in some but not all marketplaces. Measurements which have been used to determine maturity in the past, such as maximum pressure to plunger penetration in the R-1 zone and starch value, will reach a plateau in such apples and are no longer of value in determining maturation state, as the apple condition remains substantially the same in the R-1 zone while deterioration occurs internally thereof. Creep tests in the R-2 and R-3 zones indicate the internal condition of the apple's maturity which is not determinable by the present testing methods.

In an apple that has just reached maturity there will be substantially no creep in the R-1 zone and little creep interiorly of this zone. In an apple that still retains high pressure readings in the R-1 zone, with further maturity the creep will increase somewhat in the R-1 zone and will increase remarkably interiorly in the R-2 zone and especially in the R-3 zone to provide a sensitive indicator of maturation state.

The testing of fruit with the instant apparatus and method is controlled by software of the associated computer 14. The software directs a predetermined trajectory for the plunger 57 which, for ordinary testing purposes, is limited to a total displacement of the upper radius of an individual fruit 76. That radius is determined by plunger 57 position when the plunger 57 first senses the pressure of initial contact with the upper surface of a fruit 76 carried in the testing chamber 10 on the centering plate 23 by relating this position to the predetermined assumed position of the lower fruit surface resting on the centering plate 23. The type of data to be determined is preselected as pressure measurement at a constant plunger velocity, pressure measurement at a constant load or a combination of both. The test then proceeds under control of the computer software for the sensation of data at approximately 30,000 data points along the trajectory with an accuracy of at least 0.015 pound (0.25 ounce) in pressure measure.

In the test, made with a pressure measure and an interspersed measurement of creep over specific time intervals, preferably but not necessarily of about two seconds duration, the software moves the plunger 57 at a predetermined velocity as it senses constant velocity fruit pressure over a range, and then stops to measure the trajectory at a predetermined constant pressure over the predetermined time period. This sequence of measurement continues in the software predetermined manner over the entire trajectory. Creep must be measured over a period of time and in general with ordinary apples will vary substantially lineally in the range of 0.1 inch difference in a period of 2.5 seconds under a plunger load of 10 pounds, but may vary on a different functional basis for different fruit species and varieties and for these species and varieties the length of the creep measurement period becomes more important. The data sampling programs are user-determinable by programming of the controlling software, but for general use by unsophisticated users predetermined standardized programs are provided by default by the software.

The data obtained from a test is stored in computer memory for display and analysis. The data presents various possibilities for analysis to determine fruit state, Specific Juice Content, quality and maturation. The elastic modulus of the fruit may be determined. The maximum, minimum and average pressure resisting plunger penetration may be determined for an entire trajectory, in small positionally identifiable zones throughout the trajectory and in each major fruit zone. The creep deformation may be determined in similar zones individually or sequentially with or without constant velocity determination in predetermined or user determinable zones. Various comparisons of these measurements with predetermined profiles may be correlated to indicate traditionally recognized fruit conditions such as starch pattern, water core, dissolved solids and the like. In general individual samples at each data point are saved in the computer memory and are subsequently available for analysis. All of this data is valuable, especially to sophisticated testers, for determination of fruit state, past history, research and prognosis of future condition.

This data however can be massive, complex and difficult to analyze and therefore not particularly meaningful, especially to unsophisticated tester users. It has been found that a weighted assemblage of various of the data provides a simple, meaningful and quite accurate measure of present fruit condition, past fruit history and potential future development. This measure of fruit nature is denominated as the Quality Factor (QF) and is represented numerically based on a numerical scale with the 100 point designation being fruit condition at optimal picking time and the 0 point being the lower limit of acceptability as a food product. The Quality Factor (QF) values may range both above and below the 100 range as a function of time.

To determine the quality factor, data obtained in one or more tests are classified in several specific areas such as elastic modulus, pressure maxima and pressure averages for the R-1, R-2, R-3 zones, creep analysis, crispness analysis and starch and water core estimation. Each of these factors is given a numerical value based on the scale of 0 to 100, with the 100 value representing an optimal fruit at picking the 0 value representing the lower limit of consumer acceptability. The values so obtained are determined for specific fruit types and a weighted average of all factors determined to provide the quality factor. This provides a quality factor numerical value which fairly accurately quantifies the growth history and condition of a particular fruit to provide a quite accurate indication of its state of maturity, its present acceptability for economic purposes and a prediction of its additional acceptable life period. The Quality Factor (QF) values vary with species of fruit and to some degree with growing conditions, geographic growing areas and fruit history, all of which may be determined and profiled for individual fruit species and other relevant components according to methods herein described.

The Quality Factor (QF) determination is a valuable tool in determining and comparing general fruit quality especially for unsophisticated users, but it does not render the determination of its individual constituents any less valuable. The individual constituents and their relationships still serve their purposes for more sophisticated analysis.

The elastic modulus of a fruit 76 is a measure of the structural integrity of the fruit 76 Immediately after contacting the surface of a fruit 76 and before any fracture, significant deformation or actual penetration of the fruit has occurred. This elastic modulus indicates largely the structural integrity of a fruit 76 in the R-1 zone and statistically is somewhat comparable and functionally related to the average results obtained by present day regulatory intrusive type manual testers and by various non-destructive surface impingement testers.

The pressure maxima and averages within the three distinguished fruit zones R-1, R-2 and R-3 are determined from constant velocity pressure test measurements by known statistical methods. The maximum pressure determined in the R-1 zone will correspond somewhat to the pressure value given by the current industry standard manual pressure testers. This allows the instant tester data to be meaningfully compared to fruit maturity testing methods currently used in the agricultural industry and by regulators.

The average pressure measures in the R-2 zone where the bulk of the edible fruit material resides show an empirical relationship to starch value for apples and may be used for comparison with chemically determined starch values, though functional relationships vary in various fruit species. The average and maximum pressures in the R-3 core region of an apple serve as early measures indicating the maturation process and also tend to indicate structural abnormalities such as water core, spoilage or the like where these abnormalities are likely to occur.

Creep values are a measure of the viscoelastic properties of a fruit, are functionally related to crispness, and in the R-1 and R-2 zones are empirically related to average fruit pressure. Excessive creep rates tend to indicate that a fruit is nearing undesirable maturity. The creep displacement in the R-3 zone serves as a sensitive measure of the state of the maturation process or abnormalities that cause variation in the structural properties of a fruit.

Figure 8:
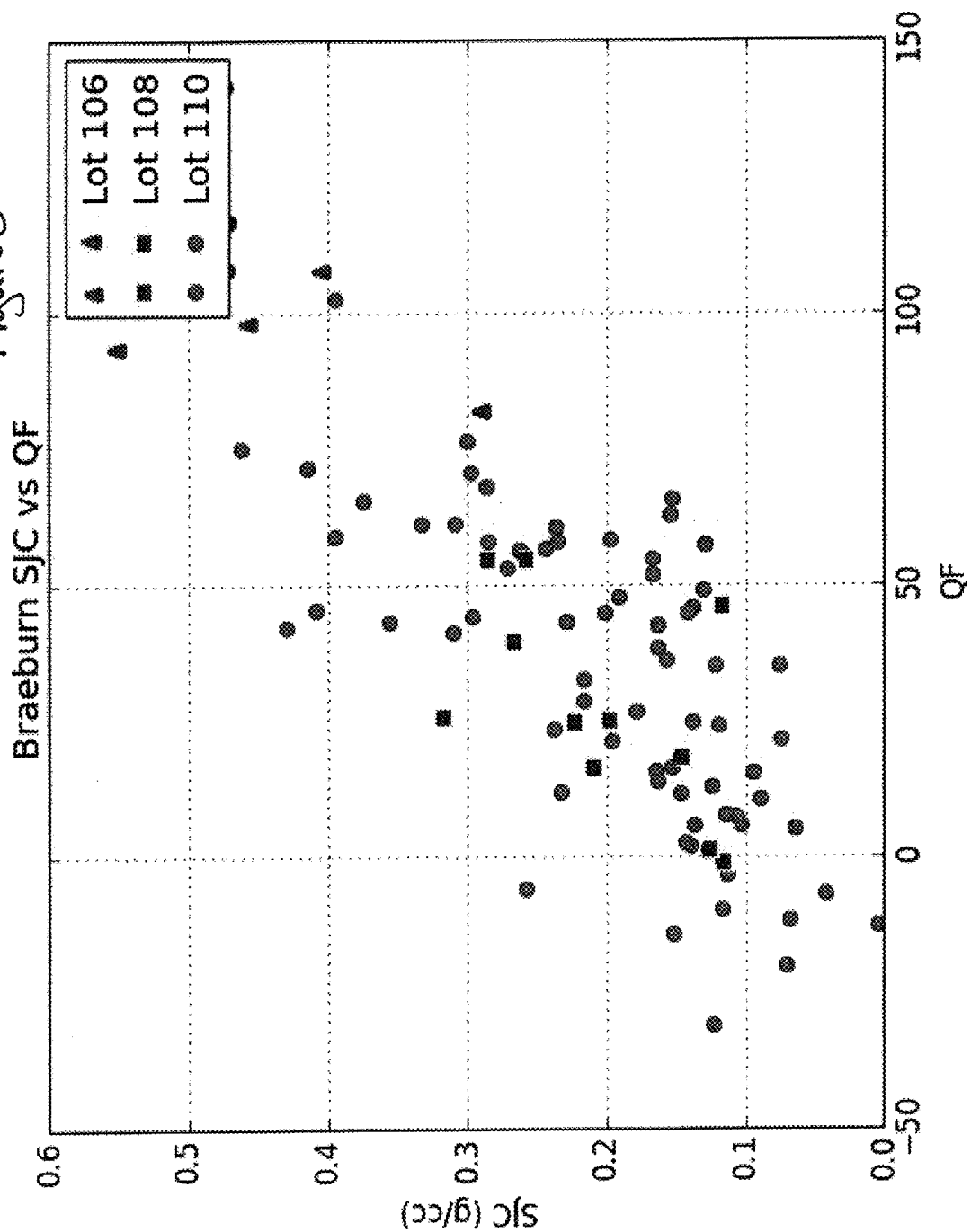
FIG. 8 is a graph of three lots of Braeburn™ apples acquired from different sources (retail and wholesale and fruit packer) showing the relationship between Specific Juice Content to QF Factor Average Firmness (A2) indicating firmer fruit has a higher Specific Juice Content.
Figure 9:
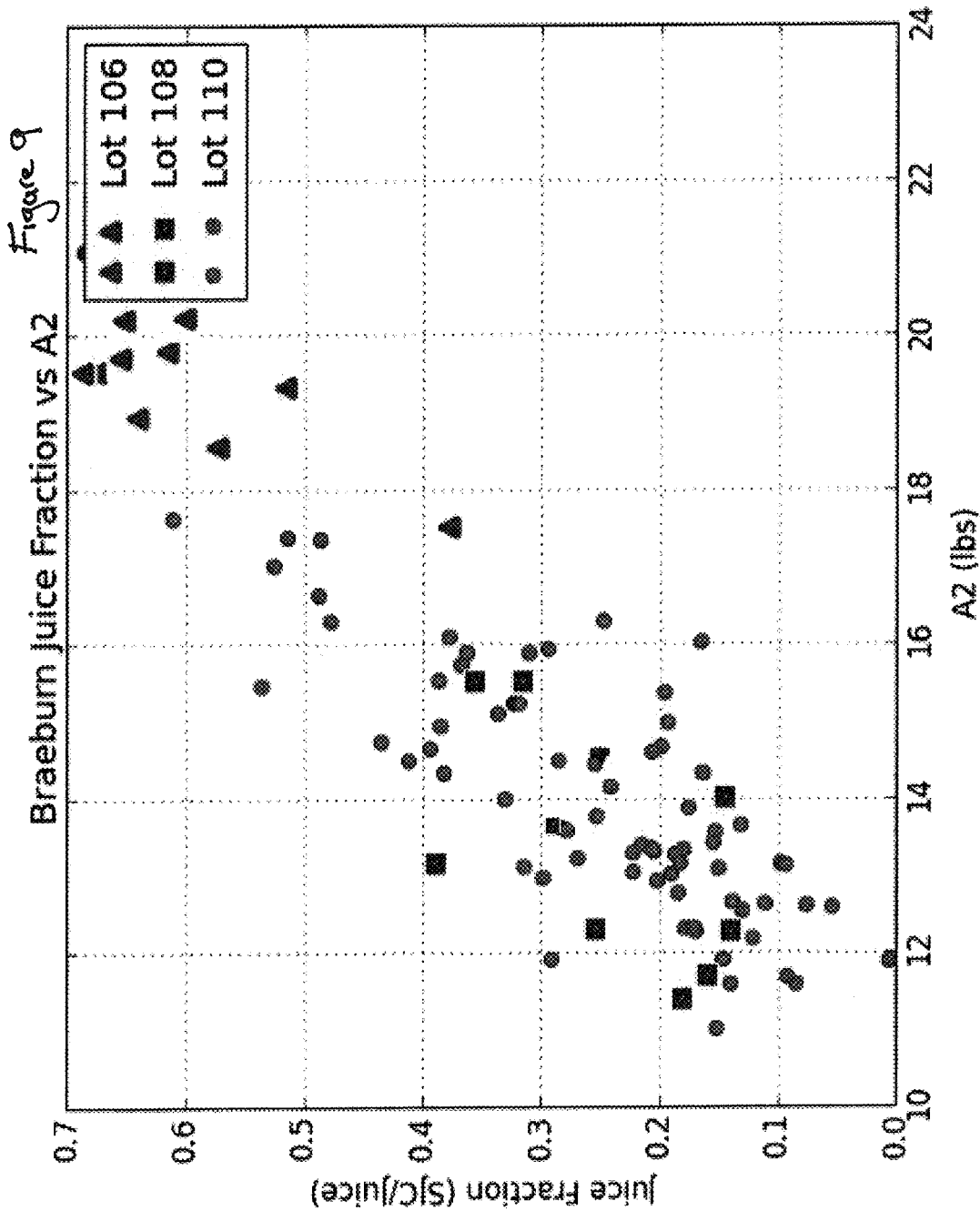
FIG. 9 is a graph of three lots of Braeburn™ apples acquired from different sources (retail and wholesale and fruit packer) showing the relationship between high Specific Juice Content and high total QF scores.

Crispness analysis determines firmness, brittleness and crunchability of the fruit meat, generally primarily in zone R-2. A portion of the high frequency force data in zone R-2 is gathered during the constant rate testing, at a rate of approximately 5000 samples per second. The software then computes an equivalent reduced sample rate of 500 samples per second to compile a finite Fourier transform from a portion of this downloaded sample data. The real portion of the computed discrete Fourier transforms sequence then is raised to the second power to represent a modified spectral density power sequence and terms of this sequence are added together into frequency power buckets which are averaged to numerically determine the crispness value. The crispness value so determined provides a numerical estimate of the desirability of fruit for consumption and is empirically related to the fruit pressure, particularly to its maximum value. Crispness analysis also serves as a secondary measure that confirms the structural quality of a fruit. Crispness is most significant at high fruit pressure, so it is a measure that is sensitive to structural changes in higher pressure apples. (See FIGS. 7, 8, 9).

A measurement of Specific Juice Content is added to the Quality Factor (QF) determination because during testing it was discovered that some of the fruit may be quite firm based on the QF measurement but did not taste good. As a result a series of taste test parameters suggested by the Washington State Apple Commission, a large number of apple QF tests were performed and paper/manual taste test evaluation forms were used as additional input for the QF determination. With additional testing it was determined that a measurement of expressed juice from the fruit is a useful additional measurement to be added to the QF determination. In the course of the tests, juice displaced from the tested fruit was collected and weighed after each test. The measurements showed that the apples with the high juice content also had high QF and in addition tasted much better scoring high taste test marks.

Previously incorporating juice content into the QF determination was not possible because of technical limitations including scale and calibration instrumentation that was not sufficiently sensitive to allow the expressed juice measurement to be added to the QF determination.

The Specific juice Content (SJC) term is a measure of the total loss of weight in juice content divided by the total volume of displacement by the penetration of a test plunger into the interior of a fruit and is measured in Units grams/$cm^3$. Total displacement is the diameter of the plunger multiplied by the total length of travel of the plunger summed over the number of tests made in a given apple.

Testing was conducted on groups of apples of varying types. Each apple was tested in four separate spots, roughly 90 degrees apart around the lateral circumference. The computer software calculates the normalized juice loss (mass difference per unit volume) for the series of tests for each apple.

The standard QF factors M, CO, CN, A2, and E2 were calculated including the maximum force in pounds measured by the plunger in the first 0.32 inches sampled (termed M1); creep number (C0) which is the distance the plunger travels into the fruit with a constant load of 10 lbs. during a set period of time usually 0.5 sec.; the average force (A2) in pounds exerted by the plunger in the second region R-2; the crispness number (CN); which is the average force (E2) in pounds exerted during the last 24 readings at the inward end of R-2. The sum of these terms is weighted to a standard Apple Quality at a scale of 100 for a perfect apple to arrive at a QF score. Quality factor (QF) is a general measure of texture and overall quality. After testing and weighing, samples were cut from the apples for a taste test to determine subjective juiciness and TILT (subjective desirability of the apple). Two testers rated the samples on a scale from 0 to 10, with 10 being the highest. (See Table A-1)

There were a total of four groups of apples tested: (See Table A-1 for a summary of all of the test results.) Two precision scales were used to provide redundancy and verification. A first precision scale called the MDT scale 100 and an external Cole-Parmer® PR 4200 (4200 g×0.01 g) scale (CPS). The conclusion was the same for both scales.

Gala™ apples from Sage Fruits, Yakima, Wash., USA, tested Aug. 28, 2013—referred to as "Gala™ 1".

Gala™ apples from Eastern Washington, USA, tested Sep. 4, 2013—referred to as "Gala™ 2".

Gala™ apples from Central Wash., USA, tested Sep. 11, 2013—referred to as "Gala™ 3".

Honeycrisp™ apples from Rainier, Wash., USA, tested Sep. 9, 2013.

The raw data, including averages and standard deviations for the Quality Factor (QF) measurements, Crisp Number (CN), Average force (A2), Max force (M1), Creep (C0), and Average force (E2) are listed in Table A-1 for each apple group. There are also averages and standard deviations for the SJC for the MDT scale 100 and CPS scale, as well as highs and lows for each sample group. The change in juice content was measured. The total volume of fruit displaced by plunger travel is calculated by determining the apple diameter and multiplying by distance of plunger travel and diameter of the plunger 57 then multiplying the product by the number of test penetrations made into the apple. In each test, four test penetrations were made.

The test data shows correlations to different fruit QF terms depending on the apple type. For example, the Galas™ evidence a good correlation between SJC and A2, and a negative correlation between SJC and C0. A higher SJC indicates more crispness, less breakdown in the cell structure and indicates a fresh apple with good taste.

For the three groups of GALA™ apples, the relationship between QF and SJC indicates the dependence of SJC on QF. There was an unknown period of time between the lots of apples being picked and tested since the lots of apples were purchased at a retail store. No data is available for pick date which would allow a determination of apple age. The tests show that lower measures of SJC also have a lower QF. Since QF has been shown to correlate directly with taste and desirability for eating the evidence confirms that dependence.

The testing done with the Honeycrisp™ apples (Table A-1) evidences a strong correlation between high SJC and a tester's TILT, suggesting the overall taste of the apple is predicted by SJC. TILT is a term coined by the inventors herein for an overall subjective taste score ranging from 1 to 10, with 10 being the best taste. The Quality Factor QF and SJC also correlate in the Honeycrisp™ group.

The CPS scale and MDT scale 100 were both tested with a calibrated mass of 0.5 g. This calibrated mass simulates juice mass lost in the test process. A dead mass near the weight of an apple was used as a sample apple. For the CPS, the dead mass used was just over 240 g. For the MDT, the dead mass used was just over 206.5 g. The combined masses simulate the apple before the test, and the dead mass alone simulates the apple after the test with juice expelled.

The process started with calibrated and dead masses (sample apple and added juice mass) placed on the scale, and the weight read after settling (about 3 seconds of no change). Both the masses were removed and then the dead mass (sample apple) was weighed alone after a delay of 10 seconds. The scale was allowed to settle. The weights were then subtracted. This test was completed 20 times for each scale. The averages and standard deviations of these tests (all measurements are in grams) are shown in Table 4.1 and Table 4.2.

TABLE 4.1

CPS LOAD CELL ACCURACY (240.13 g dead mass, 0.5 g calibrated mass)

| | calibrated mass on (g) | calibrated mass off (g) | delta weights (g) |
|---|---|---|---|
| CPS 500 mg avg | 240.6285 | 240.1265 | 0.502 |
| CPS 500 mg std dev | 0.010618 | 0.008529 | 0.012083 |

TABLE 4.2

MDT-2 LOAD CELL ACCURACY (206.63 g dead mass, 0.5 g calibrated mass)

| | calibrated mass on (g) | calibrated mass off (g) | delta weights (g) |
|---|---|---|---|
| MDT2S 500 mg avg | 207.12547 | 206.63332 | 0.492148 |
| MDT2S 500 mg std dev | 0.0460858 | 0.039027 | 0.036358 |

The assumed error used is 2σ (delta weight standard deviation). For the CPS, the 2σ is ±24.2 mg and for the MDT scale a 2σ error is ±72.7 mg. The SJC is based on the juice expressed from the fruit by the plunger 57, which is calculated by the delta weight of the apple. So to calculate accuracy of the SJC factor, an average volume displacement of 2.13875 cm3 per test was used (based on 184 individual tests; 4 per apple). Thus the Juice Factor error is approximately ±0.011299 g/cm3 using the CPS, and ±0.033999 g/cm3 using the MDT.

The foregoing description of our invention is necessarily of a detailed nature so that a specific embodiment of its best mode may be set forth as is require, but it is to be understood that various modifications of details, and rearrangement, substitution and multiplication of steps and apparatus may be resorted to without departing from its spirit, essence or scope.

Having thusly described the invention, what we desire to protect by Utility Letters Patent, and

What we claimed is:

We claim:

1. An improved method for determining the maturation state, specific juice content and condition of a fruit with an automated computer serviced intrusion type plunger tester that
   determines a volume of the fruit by measuring a distance between one surface of the fruit and a known position diametrically opposite the surface of the fruit,
   classifies a soft tissue fruit into three concentric zones consisting of a first zone extending spacedly inward from the fruit periphery, a third zone including the fruit core and a second zone bounded by the first and third zones,
   mechanically moves an elongate plunger having a known volume into the fruit through at least one data point in each of the said three zones of the fruit and determines the plunger position relative to the fruit surface at each of the data points,
   determines data relating to the viscoelastic properties of the fruit at each data point within the fruit, the improvement comprising:
   determining the weight of juice expelled from the fruit as a result of the plunger movement into and through the first and second zones and into the third zone;
   determining specific juice content of the fruit; and
   analyzing the data relating to the viscoelastic maturation state and the specific juice content to determine the condition and maturation state of the tested fruit.

2. The method of claim 1 further including the step of:
   moving the plunger into the fruit at a constant predetermined velocity and collecting at least one data point in each zone and measuring the pressure resisting plunger penetration into the fruit at the at least one data point in each zone.

3. The method of claim 1 wherein the data relating to the viscoelastic properties of the fruit is determined by:
   maintaining the plunger in the fruit at a predetermined constant pressure at at least one data point in each zone and measuring plunger motion over a predetermined period of time at the at least one data point in each zone.

4. The method of claim 1 wherein the data relating to the viscoelastic properties of the fruit is determined by:
   sequentially moving the plunger into the fruit at predetermined constant velocity and maintaining the plunger in the fruit under predetermined constant pressure for a predetermined period of time at at least one data point in each zone; and
   determining both force resisting plunger penetration and distance of plunger motion under constant pressure at the at least one data point in each zone.

5. The method of claim 1 further including the steps of:
   classifying an apple into three concentric zones comprising an R-1 zone extending from the fruit's outer peripheral surface radially inwardly to a depth of substantially 0.320 inch, an R-2 zone extending radially inwardly from the R-1 zone to an R-3 zone comprising the core area; and
   determining the plunger position and pressure resisting plunger penetration into the fruit at at least one data point in two of the three concentric zones.

6. The method of claim 1 further including the steps of:
   classifying an apple into three concentric zones comprising an R-1 zone extending from the fruit peripheral surface radially inwardly to a depth of substantially 0.320 inch, an R-2 zone extending radially inwardly from the R-1 zone to an R-3 zone and an R-3 zone comprising the core area; and determining initial plunger position, moving the plunger therefrom at a predetermined constant velocity and measuring pressure resisting plunger motion at at least one data point in at least two of the three concentric zones.

7. The method of claim 1 further including the steps of:

classifying an apple into three concentric zones comprising an R-1 zone extending from the fruit peripheral surface radially inwardly to a depth of substantially 0.320 inch, an R-2 zone extending radially inwardly from the R-1 zone to an R-3 zone and an R-3 zone comprising the core area; and determining plunger position and sequentially moving the plunger into the fruit at a predetermined constant velocity to determine pressure resisting plunger penetration and maintaining the plunger in the fruit under predetermined constant pressure for at least one predetermined period of time to determine plunger penetration under constant pressure both at at least one data point in at least two of the three concentric zones.

8. The method of claim 1 further including the step of:

determining a quality factor comprising a numerical value representing fruit condition by combining numerical values of pressure resisting plunger penetration at a predetermined constant plunger velocity and plunger penetration over a predetermined time at a constant plunger pressure as determined in at least two concentric zones of the fruit and the specific Juice content of the fruit.

9. The method of claim 8 further including the step of:

determining the quality factor by combining the numerical data in each of the at least two concentric zones of the fruit by averaging the numerical data from each zone, weighting the average of the data from at least one zone and combining the resultant averages for each zone.

10. The method of claim 1 further including the step of:

measuring frequency dependent pressure resisting plunger penetration at constant plunger velocity over a predetermined sequence of data points in at least two of the three zones; and analyzing the numeric values of frequency dependent pressure variations at the sequential data points through finite Fourier transformation to derive a numeric measure representing fruit maturity and condition from the frequency dependent pressure values for comparison with similar values derived from fruit of the same type and of predetermined condition and maturation state to determine the condition and maturation state of the tested fruit.

11. An improved automated machine for testing maturation state, specific juice content and condition of fruit, the automated machine having:

a frame enclosing a testing chamber, and carrying a power train, a plunger moved by the power train within the testing chamber to engage fruit positioned within the testing chamber, a control member carried by the frame to receive control data from a computer to operate the power train and the plunger and to sense, receive and transmit process data to the computer for analysis, display and recording, the improvement comprising:

a scale communicating within the computer to weigh the fruit before automated controlled insertion of the plunger into the fruit at at least two locations on the fruit, and to weigh the fruit after the automated controlled insertion of the plunger into the fruit at at least two locations on the fruit to determine weight change;

correlating the determined weight change with a calculated volume of the displaced fruit caused by the total plunger penetration to determine specific juice content of the fruit.

12. An improved method for automatically determining the specific juice content of a fruit comprising the steps of:

first determining the weight of the fruit and recording the weight of the fruit;

second determining the volume of the fruit;

third subjecting the fruit to a penetration test whereupon a plunger is passed into the fruit a pr determined distance from the fruit surface toward the fruit center;

fourth determining the weight of the fruit after the penetration test and recording the weight of the fruit after the penetration test;

fifth determining the change in fruit weight by comparing the before penetration test weight to the after penetration test weight;

sixth determining the volume of fruit material displaced by the plunger during the penetration test;

seventh relating the change in fruit weight to the determined volume of fruit material displaced during the penetration test;

eighth calculating the total weight of the expressed juice from the fruit; and ninth calculating specific juice content for the entire fruit volume.

* * * * *